US010358447B2

(12) United States Patent
Kakarla et al.

(10) Patent No.: US 10,358,447 B2
(45) Date of Patent: Jul. 23, 2019

(54) SUBSTITUTED 2-N-HYDROXY-1,3-DIOXO-1,2,3,4-TETRAHYDRONAPHTHYRIDINES, AND METHODS OF MAKING AND USING SAME

(71) Applicant: ARBUTUS BIOPHARMA CORPORATION, Burnaby (CA)

(72) Inventors: Ramesh Kakarla, Doylestown, PA (US); Bruce D. Dorsey, Ambler, PA (US)

(73) Assignee: Arbutus Biopharma Corporation, Burnaby, BC (CA)

( * ) Notice: Subject to any disclaimer, the term of this patent is extended or adjusted under 35 U.S.C. 154(b) by 0 days.

(21) Appl. No.: 16/204,584

(22) Filed: Nov. 29, 2018

(65) Prior Publication Data

US 2019/0169185 A1    Jun. 6, 2019

Related U.S. Application Data

(60) Provisional application No. 62/594,267, filed on Dec. 4, 2017.

(51) Int. Cl.
| | | |
|---|---|---|
| C07D 471/04 | (2006.01) | |
| A61K 31/4375 | (2006.01) | |
| A61P 31/20 | (2006.01) | |
| A61K 45/06 | (2006.01) | |

(52) U.S. Cl.
CPC ........ *C07D 471/04* (2013.01); *A61K 31/4375* (2013.01); *A61K 45/06* (2013.01); *A61P 31/20* (2018.01)

(58) Field of Classification Search
CPC . C07D 471/04; A61K 31/4375; A61K 31/519
USPC ......... 546/122; 514/300, 249, 258; 544/253, 544/349
See application file for complete search history.

(56) References Cited

FOREIGN PATENT DOCUMENTS

| WO | 2012027564 A1 | 3/2012 |
| WO | 2012085003 A1 | 6/2012 |
| WO | 2016201306 A2 | 12/2016 |
| WO | 2017161133 A1 | 9/2017 |

OTHER PUBLICATIONS

Billamboz, M. et al.: Magnesium chelating 2-hydroxyisoquinoline-1,3(2H,4H)-diones, as inhibitors of HIV-1 integrase and/or the HIV-1 reverse transcriptase ribonuclease H domain: Discovery of a novel selective inhibitor of the ribonuclease H function. Journal of Med. Chem., vol. 54, pp. 1812-1824, 2011.*
CAS Registration No. 1795464-77-5, 1,6-Naphthyridine-8-carboxamide, 6-acetyl-5,6,7,8-tetrahydro-N-methoxy-N-methyl—(accessed Nov. 2017).
CAS Registration No. 1798514-74-5, 1,6-Naphthyridine-8-carboxamide, 6-acetyl-N-butyl-5,6,7,8-tetrahydro—(accessed Nov. 2017).
CAS Registration No. 1798526-09-6, 1,6-Naphthyridine-8-carboxamide, 6-acetyl-5,6,7,8-tetrahydro-N-[3-(methylamino)-3-oxopropyl]—(accessed Nov. 2017).
CAS Registration No. 1798526-18-7, 1,6-Naphthyridine-8-carboxamide, 6-acetyl-5,6,7,8-tetrahydro-N,N-dimethyl—(accessed Nov. 2017).
CAS Registration No. 1798526-47-2, 1,6-Naphthyridine-8-carboxamide, 6-acetyl-N-ethyl-5,6,7,8-tetrahydro—(accessed Nov. 2017).
CAS Registration No. 1798620-19-5, 1,6-Naphthyridine-8-carboxamide, 6-acetyl-Ncyclopropyl-5,6,7,8-tetrahydro—(accessed Nov. 2017).
CAS Registration No. 1798620-52-6, 1,6-Naphthyridine-8-carboxamide, 6-acetyl-5,6,7,8-tetrahydro-N-(2-methylpropyl)—(accessed Nov. 2017).
CAS Registration No. 1798662-09-5, 1,6-Naphthyridine-8-carboxamide, 6-acetyl-5,6,7,8-tetrahydro-N-propyl—(accessed Nov. 2017).
CAS Registration No. 1798663-97-4, 1,6-Naphthyridine-8-carboxamide, 6-acetyl-5,6,7,8-tetrahydro-N-(3-hydroxypropyl)—(accessed Nov. 2017).
CAS Registration No. 181373-62-6, 2,7-Naphthyridine-4-carboxamide, 7-ethyl-1,2,5,6,7,8-hexahydro-3-hydroxy-1-oxo—(accessed Nov. 2017).
CAS Registration No. 1822684-75-2, 1,6-Naphthyridine-3-carboxamide, 2,3,5,6,7,8-hexahydro-2-oxo—(accessed Nov. 2017).
CAS Registration No. 1822745-78-7, 1,6-Naphthyridine-8-carboxamide, 5,6,7,8-tetrahydro-4-methyl-5,7-dioxo—(accessed Nov. 2017).
CAS Registration No. 1822910-27-9, 1,6-Naphthyridine-8-carbonitrile, 5,6,7,8-tetrahydro-2,4-dimethyl-5,7-dioxo—(accessed Nov. 2017).
CAS Registration No. 1864062-27-0, 1,6-Naphthyridine-3-carboxamide, 1,2,5,6,7,8-hexahydro-2-oxo—(accessed Nov. 2017).
CAS Registration No. 1880787-08-5, 1,6-Naphthyridine-3-carbonitrile, 6-acetyl-1,2,5,6,7,8-hexahydro-2-oxo—(accessed Nov. 2017).
CAS Registration No. 1917295-54-5, 4-Isoquinolinecarboxamide, N-cyclopropyl-1,2,3,4-tetrahydro-2-hydroxy-1,3-dioxo—(accessed Nov. 2017).
CAS Registration No. 1917295-56-7, 4-Isoquinolinecarboxamide, N-cyclohexyl-1,2,3,4-tetrahydro-2-hydroxy-1,3-dioxo—(accessed Nov. 2017).
CAS Registration No. 1935128-76-9, 1,6-Naphthyridine-8-carboxylic acid, 5,6,7,8-tetrahydro-7-oxo—(accessed Nov. 2017).
CAS Registration No. 2091594-02-2, 1,6-Naphthyridine-3-carboxylic acid, 1,2,5,6,7,8-hexahydro-4,6-dimethyl-2-oxo—(accessed Nov. 2017).

(Continued)

*Primary Examiner* — Charanjit Aulakh
(74) *Attorney, Agent, or Firm* — Saul Ewing Arnstein & Lehr LLP; Kathryn Doyle; Domingos Silva

(57) ABSTRACT

The present invention includes novel substituted 2-N-hydroxy-1,3-dioxo-1,2,3,4-tetrahydronaphthyridines, which can be used to treat or prevent hepatitis B virus (HBV) infections in a patient. In certain embodiments, the compounds and compositions of the invention inhibit HBV RNAse H activity.

24 Claims, No Drawings

(56) References Cited

OTHER PUBLICATIONS

CAS Registration No. 2104470-27-9, 1,6-Naphthyridine-8-carbonitrile, 1,2,5,6-tetrahydro-6-methyl-2,5-dioxo—(accessed Nov. 2017).
CAS Registration No. 2104567-13-5, 1,6-Naphthyridine-3-carbonitrile, 6-acetyl-1,2,5,6,7,8-hexahydro-4-methyl-2-oxo—(accessed Nov. 2017).
CAS Registration No. 2110332-90-4, 1,6-Naphthyridine-3-carbonitrile, 5,6,7,8-tetrahydro-5,7-dioxo—(accessed Nov. 2017).
CAS Registration No. 2111846-10-5, 1,6-Naphthyridine-8-carboxylic acid, 1,2,5,6-tetrahydro-6-methyl-2,5-dioxo-, methyl ester (accessed Nov. 2017).
CAS Registration No. 22851-36-1, 1,5,6,7-Tetrahydro-5,7-dioxo-4-phenyl-1,6-naphthyridine-8-carboxamide (accessed Nov. 2017).
CAS Registration No. 22851-38-3, 1,6-Naphthyridine-8-carboxamide, 1,5,6,7-tetrahydro-4-methyl-5,7-dioxo—(accessed Nov. 2017).
CAS Registration No. 331234-40-3, 2,7-Naphthyridine-4-carboxamide, 1,2,5,6,7,8-hexahydro-3-hydroxy-7-methyl-1-oxo—(accessed Nov. 2017).
CAS Registration No. 35969-69-8, 1,6-Naphthyridin-5(6H)-one, 6-hydroxy-7-methyl—(accessed Nov. 2017).
CAS Registration No. 4985-91-5, 1,5,6,7-Tetrahydro-2,4-dimethyl-5,7-dioxo-1,6-naphthyridine-8-carboxamide (accessed Nov. 2017).
CAS Registration No. 52816-57-6, 1,2-Dihydro-2-oxo-1,6-naphthyridine-3-carboxamide (accessed Nov. 2017).
CAS Registration No. 62321-89-5, 1,6-Naphthyridine-8-carbonitrile, 1,2,3,4,6,7-hexahydro-1-methyl-7-oxo—(accessed Nov. 2017).
CAS Registration No. 64500-47-6, 1,6-Naphthyridine-8-carboxamide, 1,5,6,7-tetrahydro-3,4-dimethyl-5,7-dioxo—(accessed Nov. 2017).
CAS Registration No. 66092-75-9, 1,6-Naphthyridine-3-carboxylic acid, 1-ethyl-1,4,6,7-tetrahydro-4,7-dioxo—(accessed Nov. 2017).
CAS Registration No. 74671-66-2, 1,2,3,4,6,7-Hexahydro-7-oxo-1,6-naphthyridine-8-carbonitrile (accessed Nov. 2017).
CAS Registration No. 767302-07-8, 1,6-Naphthyridine-3-carboxamide, 1,2,5,6-tetrahydro-2,5-dioxo-N,6-di-2-propen-1-yl—(accessed Nov. 2017).
CAS Registration No. 767302-11-4, 1,6-Naphthyridine-3-carboxamide, N,6-dibutyl-1,2,5,6-tetrahydro-2,5-dioxo—(accessed Nov. 2017).
CAS Registration No. 883971-57-1, 5,6-Dihydro-6-methyl-5-oxo-1,6-naphthyridine-8-carboxamide (accessed Nov. 2017).
CAS Registration No. 88752-77-6, 5,6-Dihydro-6-methyl-5-oxo-1,6-naphthyridine-8-carboxaldehyde (accessed Nov. 2017).
CAS Registration No. 88976-23-2, 5,6-Dihydro-6-methyl-5-oxo-1,6-naphthyridine-8-carboxylic acid (accessed Nov. 2017).
CAS Registration No. 911797-50-7, 1,6-Naphthyridine-8-carbonitrile, 5-amino-1,2,3,4,6,7-hexahydro-3-methyl-2,7-dioxo—(accessed Nov. 2017).
CAS Registration No. 933722-83-9, 1,2,5,6,7,8-Hexahydro-2-oxo-1,6-naphthyridine-3-carboxylic acid (accessed Nov. 2017).
Ames, et al., "Condensation of β-Dicarbonyl Compounds with Halopyridinecarboxylic acids. A Convenient Synthesis of Some Naphthyridine Derivativesderivatives," Journal of the Chemical Society, Perkin Transactions I: Organic and Bio-Organic Chemistry, 5, 1972, pp. 705-710.
Billamboz, et al., 2-hydroxyisoquinoline-1,3(2H,4H)-diones (HIDs) as human immunodeficiency virus type 1 integrase inhibitors: Influence of the alkylcarboxamide substitution of position 4, Eur J Med Chem, 117 ,2016 ,pp. 256-268.
Billamboz, et al., "4-Substituted 2-Hydroxylsoquinoline-1,3(2H,4H)-diones as a Novel Class of HIV-1 Integrase Inhibitors," ACS Med Chem Lett, 4, 2013, pp. 606-611.
Cai, et al., "Hepatitis B virus replication is blocked by a 2-hydroxyisoquinoline-1,3(2H,4H)-dione (HID) inhibitor of the viral ribonuclease H activity," Antiviral Res, 108, 2014, pp. 48-55.

Cheng, et al., "Chapter 2: The Friedlander Synthesis of Quinolines," Organic Reactions, vol. 28, 1982, pp. 37-201.
Deady, et al., Novel annulated products from aminonaphthyridinones,: Tetrahedron, vol. 62, No. 10, 2006, pp. 2313-2320.
Deady, et al., "The Reaction of Homophthalic Acid and some Aza Analogues with Vilsmeier Reagent: a Reinvestigation," J Heterocyclic Chem, vol. 38, No. 5, 2001, pp. 1185-1190.
Elnagdi, et al., "Nitriles in organic synthesis: synthesis of new polyfunctionally substituted pyridine and pyrido[3,2-c] pyridine derivatives," Gazzetta Chimica Italiana, 122(8), 1992, pp. 299-303.
Granik, et al., "Acetals of lactams and acid amides. 33. Reaction of secondary enaminoamides with amide acetals and synthesis of condensed pyrimidines," Khimiya Geterotsiklicheskikh Soedinenii, 8, 1980, pp. 1120-1124.
Granik, et al., "Acetals of lactams and acid amides. XVIII. Reactions of N,N-Dimethylformamide diethylacetal with tertiary enaminoamides and synthesis of 2-pyridone derivatives," Khimiya Geterotsiklicheskikh Soedinenii, No. 11, Nov. 1976, pp. 1509-1512.
CAS Registration No. 1309239-07-3, 1,6-Naphthyridine-3-carbonitrile, 1,2,5,6-tetrahydro-6-(3-hydroxybutyl)-2,5-dioxo—(accessed Nov. 2017).
CAS Registration No. 1312751-63-5, 1,6-Naphthyridin-5(6H)-one, 7,8-dihydro-6-methyl-, 1-oxide (accessed Nov. 2017).
CAS Registration No. 1312751-64-6, 1,6-Naphthyridin-5(6H)-one, 7,8-dihydro-6-(1-methylethyl)-, 1-oxide (accessed Nov. 2017).
CAS Registration No. 1361380-98-4, 1,6-Naphthyridine-3-carboxamide, 6-(2,2-dimethyl-1-oxopropyl)-5,6,7,8-tetrahydro-N-hydroxy—(accessed Nov. 2017).
CAS Registration No. 1383785-16-7, 4-Isoquinolinecarboxamide, N-(3-chloropropyl)-1,2,3,4-tetrahydro-2-hydroxy-1,3-dioxo—(accessed Nov. 2017).
CAS Registration No. 1383785-17-8, 1,2,3,4-Tetrahydro-2-hydroxy-1,3-dioxo-N-propyl-4-isoquinolinecarboxamide (accessed Nov. 2017).
CAS Registration No. 1383785-18-9, N-Butyl-1,2,3,4-tetrahydro-2-hydroxy-1,3-dioxo-4-isoquinolinecarboxamide (accessed Nov. 2017).
CAS Registration No. 1383785-19-0, 1,2,3,4-Tetrahydro-2-hydroxy-1,3-dioxo-N-pentyl-4-isoquinolinecarboxamide (accessed Nov. 2017).
CAS Registration No. 1383785-20-3, N-Hexyl-1,2,3,4-tetrahydro-2-hydroxy-1,3-dioxo-4-isoquinolinecarboxamide (accessed Nov. 2017).
CAS Registration No. 1383785-21-4, 1,2,3,4-Tetrahydro-2-hydroxy-N-nonyl-1,3-dioxo-4-isoquinolinecarboxamide (accessed Nov. 2017).
CAS Registration No. 1383785-22-5, 1,2,3,4-Tetrahydro-2-hydroxy-N-(1-methylethyl)-1,3-dioxo-4-isoquinolinecarboxamide (accessed Nov. 2017).
CAS Registration No. 1383785-23-6, N-(1,1-Dimethylethyl)-1,2,3,4-tetrahydro-2-hydroxy-1,3-dioxo-4-isoquinolinecarboxamide (accessed Nov. 2017).
CAS Registration No. 1383785-24-7, N-Cyclopentyl-1,2,3,4-tetrahydro-2-hydroxy-1,3-dioxo-4-isoquinolinecarboxamide (accessed Nov. 2017).
CAS Registration No. 1383785-25-8, 4-Isoquinolinecarboxamide, 1,2,3,4-tetrahydro-2-hydroxy-1,3-dioxo-N-2-propen-1-yl—(accessed Nov. 2017).
CAS Registration No. 1383785-30-5, 1,2,3,4-Tetrahydro-2-hydroxy-N-[(4-methylphenyl)methyl]-1,3-dioxo-4-isoquinolinecarboxamide (accessed Nov. 2017).
CAS Registration No. 1383785-32-7, N-[(2,4-Dihydroxyphenyl)methyl]-1,2,3,4-tetrahydro-2-hydroxy-1,3-dioxo-4-isoquinolinecarboxamid (accessed Nov. 2017).
CAS Registration No. 1383785-38-3, 2-Hydroxy-4-(1-piperidinylcarbonyl)-1,3(2H,4H)-isoquinolinedione (accessed Nov. 2017).
CAS Registration No. 1383785-41-8, N,N-Diethyl-1,2,3,4-tetrahydro-2-hydroxy-1,3-dioxo-4-isoquinolinecarboxamide (accessed Nov. 2017).
CAS Registration No. 1383785-46-3, N-Heptyl-1,2,3,4-tetrahydro-2-hydroxy-1,3-dioxo-4-isoquinolinecarboxamide (accessed Nov. 2017).
CAS Registration No. 1383785-49-6, 1,2,3,4-Tetrahydro-2-hydroxy-N-octyl-1,3-dioxo-4-isoquinolinecarboxamide (accessed Nov. 2017).
CAS Registration No. 1383785-50-9, 4-Isoquinolinecarboxamide, N-dodecyl-1,2,3,4-tetrahydro-2-hydroxy-1,3-dioxo—(accessed Nov. 2017).
CAS Registration No. 1383785-51-0, 1,2,3,4-Tetrahydro-2-hydroxy-1,3-dioxo-N-phenyl-4-isoquinolinecarboxamide (accessed Nov. 2017).

(56) References Cited

OTHER PUBLICATIONS

CAS Registration No. 1383785-54-3, 1,2,3,4-Tetrahydro-2-hydroxy-1,3-dioxo-N-(phenylmethyl)-4-isoquinolinecarboxamide (accessed Nov. 2017).

CAS Registration No. 1383786-33-1, 4-Isoquinolinecarboxylic acid, 7-(acetylamino)-1,2,3,4-tetrahydro-1,3-dioxo-2-(phenylmethoxy)-, methyl ester (accessed Nov. 2017).

CAS Registration No. 1383786-41-1, 4-Isoquinolinecarboxylic acid, 1,2,3,4-tetrahydro-1,3-dioxo-7-[(2-phenylacetyl) amino]-2-(phenylmethoxy)-, methyl ester (accessed Nov. 2017).

CAS Registration No. 1383786-46-6, 4-Isoquinolinecarboxylic acid, 7-(benzoylamino)-1,2,3,4-tetrahydro-1,3-dioxo-2-(phenylmethoxy)-, methyl ester (accessed Nov. 2017).

CAS Registration No. 145664-42-2, 1,6-Naphthyridine-3,8-dicarbonitrile, 2-amino-5,6,7,8-tetrahydro-5,7-dioxo—(accessed Nov. 2017).

CAS Registration No. 1456704-02-1, 1,6-Naphthyridin-5(6H)-one, 8-(1-hydroxy-1-methylethyl)-, 1-oxide (accessed Nov. 2017).

CAS Registration No. 14903-72-1, 1,2,5,6,7,8-Hexahydro-6-methyl-2-oxo-1,6-naphthyridine-3-carboxylic acid (accessed Nov. 2017).

CAS Registration No. 1500209-23-3, 1,6-Naphthyridine-3-carboxaldehyde, 1,2,5,6,7,8-hexahydro-6-methyl-2-oxo—(accessed Nov. 2017).

CAS Registration No. 1504346-21-7, 1,6-Naphthyridine-3-carbonitrile, 5,6,7,8-tetrahydro-4-methyl-5,7-dioxo—(accessed Nov. 2017).

CAS Registration No. 1505371-23-2, 1,6-Naphthyridine-5,7(6H,8H)-dione, 3-(aminomethyl)-4-methyl—(accessed Nov. 2017).

CAS Registration No. 1507270-30-5, 1,6-Naphthyridine-3-carboxylic acid, 1,2,5,6,7,8-hexahydro-6-methyl-2-oxo-, hydrazide (accessed Nov. 2017).

CAS Registration No. 1512728-47-0, 1,6-Naphthyridine-8-carboxylic acid, 1,2,5,6-tetrahydro-6-methyl-2,5-dioxo—(accessed Nov. 2017).

CAS Registration No. 1518118-21-2, 1,6-Naphthyridine-3-carboxylic acid, 5,6,7,8-tetrahydro-5,7-dioxo—(accessed Nov. 2017).

CAS Registration No. 1521205-17-3, 1,6-Naphthyridin-2(1H)-one, 5,6,7,8-tetrahydro-3-(hydroxymethyl)-6-methyl—(accessed Nov. 2017).

CAS Registration No. 1534483-56-1, 1,6-Naphthyridine-3-carboxylic acid, 6-acetyl-1,2,5,6,7,8-hexahydro-2-oxo—(accessed Nov. 2017).

CAS Registration No. 1540945-47-8, 1,6-Naphthyridine-3-carboxylic acid, 6-ethyl-1,2,5,6,7,8-hexahydro-2-oxo-, hydrazide (accessed Nov. 2017).

CAS Registration No. 1542727-34-3, 1,6-Naphthyridine-3-carboxylic acid, 5,6,7,8-tetrahydro-4-methyl-5,7-dioxo—(accessed Nov. 2017) ,2017.

CAS Registration No. 1553834-58-4, 1,6-Naphthyridine-8-carbonitrile, 5-amino-1,2,3,4,6,7-hexahydro-2,7-dioxo—(accessed Nov. 2017).

CAS Registration No. 1787944-26-6, 1,6-Naphthyridine-8-carboxamide, 6-acetyl-5,6,7,8-tetrahydro-N-(1-methylpropyl)—(accessed Nov. 2017).

CAS Registration No. 1787947-53-8, 1,6-Naphthyridine-8-carboxamide, 6-acetyl-5,6,7,8-tetrahydro-N-(2-hydroxyethyl)—(accessed Nov. 2017).

CAS Registration No. 1787947-55-0, 1,6-Naphthyridine-8-carboxamide, 6-acetyl-5,6,7,8-tetrahydro-N-(1-methylethyl)—(accessed Nov. 2017).

CAS Registration No. 1788700-83-3, 1,6-Naphthyridine-8-carboxamide, 6-acetyl-N,Ndiethyl-5,6,7,8-tetrahydro-—(accessed Nov. 2017).

CAS Registration No. 1788701-22-3, 1,6-Naphthyridine-8-carboxamide, 6-acetyl-N-(1,1-dimethylethyl)-5,6,7,8-tetrahydro—(accessed Nov. 2017).

CAS Registration No. 1795210-94-4, 1,6-Naphthyridine-8-carboxamide, 6-acetyl-5,6,7,8-tetrahydro-N-methyl—(accessed Nov. 2017).

CAS Registration No. 1795220-88-0, 1,6-Naphthyridine-8-carboxamide, 6-acetyl-5,6,7,8-tetrahydro-N-(1-methylbutyl)—(accessed Nov. 2017).

CAS Registration No. 1795425-48-7, 1,6-Naphthyridine-8-carboxylic acid, 6-acetyl-5,6,7,8-tetrahydro-, 2,2-dimethylhydrazide (accessed Nov. 2017).

CAS Registration No. 1795446-50-2, 1,6-Naphthyridine-8-carboxamide, 6-acetyl-5,6,7,8-tetrahydro-N-[3-[(1-methylethyl)amino]-3-oxopropyl] (accessed Nov. 2017).

CAS Registration No. 1795464-45-7, 1,6-Naphthyridine-8-carboxamide, 6-acetyl-5,6,7,8-tetrahydro-N-2-propen-1-yl—(accessed Nov. 2017).

Granik, et al., Acetals of lactams and acid amides. XXIII. Kinetics of the cyclization of N,N-dimethyl-N'-[α-cyano-β-(dimethylamino) crotonoyl]formamidine, its five-, six-, and seven-membered analogs, and N-methyl-2-[[α-cyano-β-(dimethylamino)acryloyl] imino]piperidin, Khimiya Geterotsiklicheskikh Soedinenii, 11 ,1977 ,pp. 1523-1526.

Granik, et al., Acetals of lactams and amides of acids. 35. Synthesis of condensed bi- and tricyclic pyridines from enamino amides, Khimiya Geterotsiklicheskikh Soedinenii, No. 4 ,1982 ,pp. 518-522.

Granik, et al., Rearrangement of a derivative of pyrido[1,2-c]pyrimidine into substituted 1,6-naphthyridine, Khimiya Geterotsiklicheskikh Soedinenii, No. 3 ,1980 ,pp. 416-417.

Haglid, et al., Syntheses of tetrahydronaphthyridines, Arkiv foer Kemi, 26(41) ,1967 ,pp. 489-495.

Hawes, et al., 1,6-Naphthyridines. II. 2,3-Disubstituted derivatives and some new tricyclic ring systems, Journal of Heterocyclic Chemistry, 11(2) ,Apr. 1974 ,pp. 151-155.

Huckins, et al., Rh(III)-Catalyzed C—H Activation and Double Directing Group Strategy for the Regioselective Synthesis of Naphthyridinones, Journal of the American Chemical Society, 135(39) ,2013 ,pp. 14492-14495.

Jhalani, et al., A Convenient Synthesis of 5-Keto-6-methyl-5,6-dihydro-1,6-naphthyridine, Indian J Chem, vol. 22B, No. 9 ,1983 ,pp. 916.

Jhalani, et al., Synthesis of naphthyridinones from pyrano[4, 3-b]pyridin-5-one: a convenient synthesis of 5, 6-hydro-5-oxo-7-methylpyrano [4, 3-b]pyridine, Indian Drugs, 20(12) ,Sep. 1983 ,pp. 482-486.

Jones, et al., Chapter 2: The Vilsmeier reaction of non-aromatic compounds, Organic Reactions, vol. 56 ,2000 ,pp. 355-659.

Junek, et al., Beitrage zur Chemie der Enaminoketone, 1. Mitt: Eine Synthese von 1,6-Naphthyridin-Derivaten, Monatschefte fur Chemie, 100 ,1969 ,pp. 570-575.

Junek, et al., Report on the chemistry of enaminoketones, part 13, Syntheses of alkyl-, cycloalkylpyridines, and naphthyridines, Monatshefte fuer Chemie, 108(3) ,1977 ,pp. 689-702.

Junek, et al., Syntheses with nitriles. 28. Ritter reaction, Monatshefte fur Chemie, 101(4) ,1970 ,pp. 1234-1242.

Junek, et al., Syntheses with nitriles. XI. Hydrolysis products of cyano dihydropyridines, Monatshefte fuer Chemie, 96(6) ,1965 ,pp. 2046-2050.

Junek, et al., Syntheses with nitriles. XXV. Direct synthesis of 1,6-naphthyridinediones from enamino ketones and dimeric malonitrile, Tetrahedron Letters, 29 ,1969 ,pp. 2439-2440.

Meth-Cohn, et al., Pyridine annelation of o-methylarylcarboxylic acids with Vilsmeier reagents, Tetrahedron Letters, vol. 24, No. 42 ,1983 ,pp. 4607-4610.

Paronikyan, et al., Synthesis and antiarrhythmic activity of 7-benzyl(ethyl)-1-hdyroxy-4-carbamoyl-3-oxo-5,6-dihydro-8H-2,7-naphthyridines, Pharmaceutical Chemistry Journal, vol. 30, No. 6 (translated from Khimiko-Farmatsevticheskii Zhurnal, vol. 30, No. 6, pp. 13-15) ,1996 ,pp. 365-367.

Phuan, et al., Product class 8: Naphthyridines, Science of Synthesis, 15 ,2005 ,pp. 947-985.

Prostakov, et al., Substituted pyridines. 5-Methyl-2-formylpyridine and 5-methyl-4-phenyl-2-formylpyridine, Khimiya Geterotsiklicheskikh Soedinenii, No. 5 ,1965 ,pp. 738-743.

Sams, et al., Efficacy switching SAR of mGluR5 allosteric modulators: Highly potent positive and negative modulators from one chemotype, Bioorganic & Medicinal Chemistry Letters, vol. 21, No. 11 ,2011 ,pp. 3407-3410.

(56) References Cited

OTHER PUBLICATIONS

Strehlke, et al., "Studies on the antibacterial activity of quinolone carboxylic acids. VII. Aza analogs. A new synthesis of antibacterial 1,7-disubstituted 1,4-dihydro-4-oxo-1,6-naphthyridine-3-carboxylic acids," Eur J Med Chem, vol. 12, No. 6, 1977, pp. 541-547.

Suchaud, et al., Investigation of a Novel Series of 2-Hydroxyisoquinoline-1,3(2H,4H)-diones as Human Immunodeficiency Virus Type 1 Integrase Inhibitors, J Med Chem, 57 ,2014 ,pp. 4640-4660.

Victory, et al., A synthesis of 1,2,3,4-tetrahydro-1,6-naphthyridines, Heterocycles, vol. 34, No. 10 ,1992 ,pp. 1905-1916.

* cited by examiner

SUBSTITUTED 2-N-HYDROXY-1,3-DIOXO-1,2,3,4-TETRAHYDRONAPHTHYRIDINES, AND METHODS OF MAKING AND USING SAME

CROSS-REFERENCE TO RELATED APPLICATION

The present application claims priority under 35 U.S.C. § 119(e) to U.S. Provisional Patent Application No. 62/594,267, filed Dec. 4, 2017, which application is hereby incorporated herein by reference in its entirety.

BACKGROUND OF THE INVENTION

Hepatitis B is one of the world's most prevalent diseases, being listed by National Institute of Allergy and Infectious Diseases (NIAID) as a High Priority Area of Interest. Although most individuals resolve the infection following acute symptoms, approximately 30% of cases become chronic. 350-400 million people worldwide are estimated to have chronic hepatitis B, leading to 0.5-1 million deaths per year, due largely to the development of hepatocellular carcinoma, cirrhosis and/or other complications.

HBV is a noncytopathic, liver tropic DNA virus belonging to Hepadnaviridae family. Pregenomic (pg) RNA is the template for reverse transcriptional replication of HBV DNA. Reverse transcription for HBV is catalyzed by a virally-encoded polymerase that has two enzymatic activities: a DNA polymerase that synthesizes new DNA, and a ribonuclease H (RNAse H) that destroys the viral RNA after it has been copied into DNA. Both activities are essential for viral replication.

A limited number of drugs are currently approved for the management of chronic hepatitis B, including two formulations of alpha-interferon (standard and pegylated) and five nucleoside/nucleotide analogues (lamivudine, adefovir, entecavir, telbivudine, and tenofovir) that inhibit hepatitis B virus (HBV) DNA polymerase. At present, the first-line treatment choices are entecavir, tenofovir or peg-interferon alfa-2a. However, peg-interferon alfa-2a achieves desirable serological milestones in only one third of treated patients, and is often associated with severe side effects. Entecavir and tenofovir are potent HBV inhibitors, but require long-term or possibly lifetime administration to continuously suppress HBV replication, and may eventually fail due to emergence of drug-resistant viruses.

There is a need in the art for the identification of novel, safe, and effective therapies for hepatitis B. In certain embodiments, the novel compounds should inhibit RNAse H activity. In other embodiments, the novel compounds can be used in patients that are HBV infected, patients who are at risk of becoming HBV infected, and/or patients that are infected with drug-resistant HBV. The present invention addresses this need.

BRIEF SUMMARY OF THE INVENTION

The invention provides a compound of the invention. The invention further provides a pharmaceutical composition comprising at least one compound of the invention and a pharmaceutically acceptable carrier. The invention further provides a method of treating or preventing hepatitis virus infection in a subject. The invention further provides a method of inhibiting RNAse H activity in a HBV-infected subject.

In certain embodiments, the compound is of formula (I):

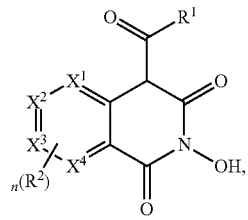

wherein: $R^1$ is selected from the group consisting of —OR' and —NR'R', wherein each occurrence of R' is independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted benzyl, optionally substituted aryl, and optionally substituted heteroaryl; each of $X^1$, $X^2$, $X^3$, and $X^4$ is independently selected from the group consisting of N and $CR^3$, with the proviso that 1-2 of $X^1$, $X^2$, $X^3$, and $X^4$ are N; $R^2$ and $R^3$ are independently selected from the group consisting of H, $C_1$-$C_6$ alkyl, $C_1$-$C_6$ haloalkyl, $C_1$-$C_6$ haloalkoxy, halo, —CN, —OR", —NR"R", —N($C_0$-$C_6$ alkyl)C(=O)R", —N($C_0$-$C_6$ alkyl)S(=O)$_2$R", —NO$_2$, —S(=O)$_2$NR"R", —OC(=O)R", and —C(=O)O—$C_1$-$C_6$ alkyl, wherein each occurrence of R" is independently selected from the group consisting of H, optionally substituted $C_1$-$C_6$ alkyl, optionally substituted $C_3$-$C_8$ cycloalkyl, and optionally substituted phenyl; and n is 0, 1, 2, 3, or 4; or a salt, solvate, geometric isomer, stereoisomer, tautomer, or any mixtures thereof.

In certain embodiments, each occurrence of alkyl, alkenyl, alkynyl, or cycloalkyl is independently optionally substituted with at least one substituent selected from the group consisting of $C_1$-$C_6$ alkyl, halo, keto (C=O), —OR, optionally substituted phenyl, optionally substituted heteroaryl, optionally substituted heterocyclyl, —N(R)(R), —N(R)—(C=O)R, —C(=O)R, —C(=O)(optionally substituted phenyl), —C(=O)(optionally substituted heteroaryl), —C(=O)N(R)(R), —C(=O)(CH$_2$)$_{0-3}$OR, —S(=O)$_2$R, and —SO$_2$N(R)(R), wherein each occurrence of R is independently selected from the group consisting of H, $C_1$-$C_6$ alkyl, and $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R)(R), —NO$_2$, —S(=O)$_2$N(R)(R), acyl, and $C_1$-$C_6$ alkoxycarbonyl, wherein each occurrence of R is independently selected from the group consisting of H, $C_1$-$C_6$ alkyl, and $C_3$-$C_8$ cycloalkyl.

In certain embodiments, each occurrence of aryl or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R)(R), and $C_1$-$C_6$ alkoxycarbonyl, wherein each occurrence of R is independently selected from the group consisting of H, $C_1$-$C_6$ alkyl, and $C_3$-$C_8$ cycloalkyl.

In certain embodiments, the compound is at least one selected from the group consisting of:

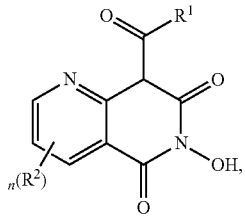
(Ia)

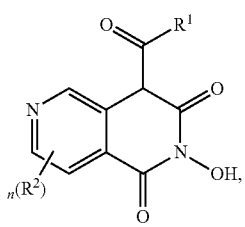
(Ib)

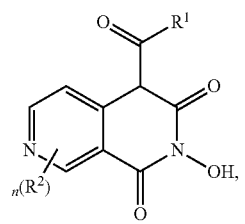
(Ic)

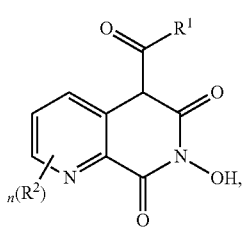
(Id)

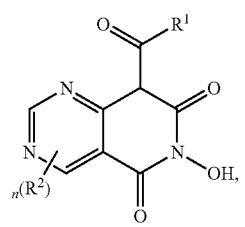
(Ie)

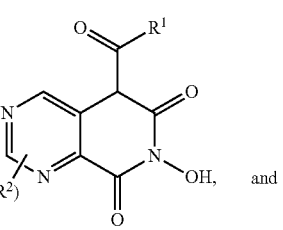
(If)

and

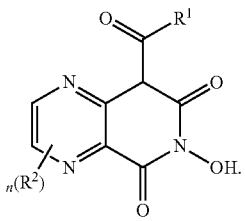
(Ig)

In certain embodiments, the compound is

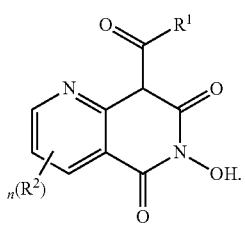
(Ia)

In certain embodiments, the compound is selected from the group consisting of: Ethyl 6-hydroxy-2-methoxy-5,7-dioxo-5,6,7,8-tetrahydro-1,6-naphthyridine-8-carboxylate; N,N-diethyl-6-hydroxy-2-methoxy-5,7-dioxo-5,6,7,8-tetrahydro-1,6-naphthyridine-8-carboxamide; N-(4-chlorophenyl)-6-hydroxy-2-methoxy-5,7-dioxo-5,6,7,8-tetrahydro-1,6-naphthyridine-8-carboxamide; N-(4-fluorophenyl)-6-hydroxy-2-methoxy-5,7-dioxo-5,6,7,8-tetrahydro-1,6-naphthyridine-8-carboxamide; N-(4-Chlorobenzyl)-6-dihydroxy-2-methoxy-5,7-dioxo-5,6,7,8-tetrahydro-1,6-naphthyridine-8-carboxamide; N-(4-fluorobenzyl)-2,6-dihydroxy-5,7-dioxo-5,6,7,8-tetrahydro-1,6-naphthyridine-8-carboxamide; N-(4-Methoxybenzyl)-2,6-dihydroxy-5,7-dioxo-5,6,7,8-tetrahydro-1,6-naphthyridine-8-carboxamide; or a salt, solvate, geometric isomer, stereoisomer, tautomer, or any mixtures thereof.

In certain embodiments, the composition further comprises at least one additional agent useful for treating hepatitis infection. In certain embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator.

In certain embodiments, the method comprises administering to the subject in need thereof a therapeutically effective amount of at least one compound of the invention. In certain embodiments, the at least one compound is administered to the subject in a pharmaceutically acceptable composition.

In certain embodiments, the subject is further administered at least one additional agent useful for treating the hepatitis infection. In certain embodiments, the subject is further administered at least one additional agent useful for treating the HBV infection. In certain embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In certain embodiments, the subject is co-administered the at least one compound and the at least one additional agent. In certain embodiments, the at least one compound and the at least one additional agent are coformulated.

In certain embodiments, the virus comprises hepatitis B virus (HBV).

In certain embodiments, the subject is a mammal. In certain embodiments, the mammal is a human.

DETAILED DESCRIPTION OF THE INVENTION

The invention relates, in certain aspects, to the discovery of certain substituted 2-N-hydroxy-1,3-dioxo-1,2,3,4-tetrahydronaphthyridines that are useful to treat and/or prevent HBV infection and related conditions in a subject. In certain embodiments, the compounds of the invention are RNAse H inhibitors.

Definitions

As used herein, each of the following terms has the meaning associated with it in this section. Unless defined otherwise, all technical and scientific terms used herein generally have the same meaning as commonly understood by one of ordinary skill in the art to which this invention belongs. Generally, the nomenclature used herein and the laboratory procedures in animal pharmacology, pharmaceutical science, separation science and organic chemistry are those well-known and commonly employed in the art. It should be understood that the order of steps or order for performing certain actions is immaterial, so long as the present teachings remain operable. Moreover, two or more steps or actions can be conducted simultaneously or not.

As used herein, the articles "a" and "an" refer to one or to more than one (i.e., to at least one) of the grammatical object of the article. By way of example, "an element" means one element or more than one element.

As used herein, the term "alkenyl," employed alone or in combination with other terms, means, unless otherwise stated, a stable monounsaturated or diunsaturated straight chain or branched chain hydrocarbon group having the stated number of carbon atoms. Examples include vinyl, propenyl (or allyl), crotyl, isopentenyl, butadienyl, 1,3-pentadienyl, 1,4-pentadienyl, and the higher homologs and isomers. A functional group representing an alkene is exemplified by —CH$_2$—CH=CH$_2$.

As used herein, the term "alkoxy" employed alone or in combination with other terms means, unless otherwise stated, an alkyl group having the designated number of carbon atoms, as defined elsewhere herein, connected to the rest of the molecule via an oxygen atom, such as, for example, methoxy, ethoxy, 1-propoxy, 2-propoxy (or isopropoxy) and the higher homologs and isomers. A specific example is (C$_1$-C$_3$)alkoxy, such as, but not limited to, ethoxy and methoxy.

As used herein, the term "alkyl" by itself or as part of another substituent means, unless otherwise stated, a straight or branched chain hydrocarbon having the number of carbon atoms designated (i.e., C$_1$-C$_{10}$ means one to ten carbon atoms) and includes straight, branched chain, or cyclic substituent groups. Examples include methyl, ethyl, propyl, isopropyl, butyl, isobutyl, tent-butyl, pentyl, neopentyl, hexyl, and cyclopropylmethyl. A specific embodiment is (C$_1$-C$_6$)alkyl, such as, but not limited to, ethyl, methyl, isopropyl, isobutyl, n-pentyl, n-hexyl and cyclopropylmethyl.

As used herein, the term "alkynyl" employed alone or in combination with other terms means, unless otherwise stated, a stable straight chain or branched chain hydrocarbon group with a triple carbon-carbon bond, having the stated number of carbon atoms. Non-limiting examples include ethynyl and propynyl, and the higher homologs and isomers. The term "propargylic" refers to a group exemplified by —CH$_2$—C≡CH. The term "homopropargylic" refers to a group exemplified by —CH$_2$CH$_2$—C≡CH.

As used herein, the term "aromatic" refers to a carbocycle or heterocycle with one or more polyunsaturated rings and having aromatic character, i.e., having (4n+2) delocalized π(pi) electrons, where 'n' is an integer.

As used herein, the term "aryl" employed alone or in combination with other terms means, unless otherwise stated, a carbocyclic aromatic system containing one or more rings (typically one, two or three rings) wherein such rings may be attached together in a pendent manner, such as a biphenyl, or may be fused, such as naphthalene. Examples include phenyl, anthracyl and naphthyl. Aryl groups also include, for example, phenyl or naphthyl rings fused with one or more saturated or partially saturated carbon rings (e.g., bicyclo[4.2.0]octa-1,3,5-trienyl, or indanyl), which can be substituted at one or more carbon atoms of the aromatic and/or saturated or partially saturated rings.

As used herein, the term "aryl-(C$_1$-C$_6$)alkyl" refers to a functional group wherein a one to six carbon alkylene chain is attached to an aryl group, e.g., —CH$_2$CH$_2$-phenyl or —CH$_2$-phenyl (or benzyl). Specific examples are aryl-CH$_2$— and aryl-CH(CH$_3$)—. The term "substituted aryl-(C$_1$-C$_6$)alkyl" refers to an aryl-(C$_1$-C$_6$)alkyl functional group in which the aryl group is substituted. A specific example is substituted aryl-(CH$_2$)—. Similarly, the term "heteroaryl-(C$_1$-C$_6$)alkyl" refers to a functional group wherein a one to three carbon alkylene chain is attached to a heteroaryl group, e.g., —CH$_2$CH$_2$-pyridyl. A specific example is heteroaryl-(CH$_2$)—. The term "substituted heteroaryl-(C$_1$-C$_6$)alkyl" refers to a heteroaryl-(C$_1$-C$_6$)alkyl functional group in which the heteroaryl group is substituted. A specific example is substituted heteroaryl-(CH$_2$)—.

In one aspect, the terms "co-administered" and "co-administration" as relating to a subject refer to administering to the subject a compound and/or composition of the invention along with a compound and/or composition that may also treat or prevent a disease or disorder contemplated herein. In certain embodiments, the co-administered compounds and/or compositions are administered separately, or in any kind of combination as part of a single therapeutic approach. The co-administered compound and/or composition may be formulated in any kind of combinations as mixtures of solids and liquids under a variety of solid, gel, and liquid formulations, and as a solution.

As used herein, the term "cycloalkyl" by itself or as part of another substituent refers to, unless otherwise stated, a cyclic chain hydrocarbon having the number of carbon atoms designated (i.e., C$_3$-C$_6$ refers to a cyclic group comprising a ring group consisting of three to six carbon atoms) and includes straight, branched chain or cyclic substituent groups. Examples of (C$_3$-C$_6$)cycloalkyl groups are cyclopropyl, cyclobutyl, cyclopentyl and cyclohexyl. Cycloalkyl rings can be optionally substituted. Non-limiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydro azulenyl; bicyclo[6.2.0]decanyl, decahydronaphthalenyl, and dodecahydro-1H- fluorenyl. The term "cycloalkyl" also includes bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

As used herein, a "disease" is a state of health of a subject wherein the subject cannot maintain homeostasis, and wherein if the disease is not ameliorated then the subject's health continues to deteriorate.

As used herein, a "disorder" in a subject is a state of health in which the subject is able to maintain homeostasis, but in which the subject's state of health is less favorable than it would be in the absence of the disorder. Left untreated, a disorder does not necessarily cause a further decrease in the subject's state of health.

As used herein, the term "halide" refers to a halogen atom bearing a negative charge. The halide anions are fluoride ($F^-$), chloride ($CF^-$), bromide ($Br^-$), and iodide ($I^-$).

As used herein, the term "halo" or "halogen" alone or as part of another substituent refers to, unless otherwise stated, a fluorine, chlorine, bromine, or iodine atom.

As used herein, the term "heteroalkenyl" by itself or in combination with another term refers to, unless otherwise stated, a stable straight or branched chain monounsaturated or diunsaturated hydrocarbon group consisting of the stated number of carbon atoms and one or two heteroatoms selected from the group consisting of O, N, and S, and wherein the nitrogen and sulfur atoms may optionally be oxidized and the nitrogen heteroatom may optionally be quaternized. Up to two heteroatoms may be placed consecutively. Examples include —CH=CH—O—CH$_3$, —CH=CH—CH$_2$—OH, —CH$_2$—CH=N—OCH$_3$, —CH=CH—N(CH$_3$)—CH$_3$, and —CH$_2$—CH=CH—CH$_2$—SH.

As used herein, the term "heteroalkyl" by itself or in combination with another term refers to, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —OCH$_2$CH$_2$CH$_3$, —CH$_2$CH$_2$CH$_2$OH, —CH$_2$CH$_2$NHCH$_3$, —CH$_2$SCH$_2$CH$_3$, and —CH$_2$CH$_2$S(=O)CH$_3$. Up to two heteroatoms may be consecutive, such as, for example, —CH$_2$NH—OCH$_3$, or —CH$_2$CH$_2$SSCH$_3$.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl.

As used herein, the term "heterocycle" or "heterocyclyl" or "heterocyclic" by itself or as part of another substituent refers to, unless otherwise stated, an unsubstituted or substituted, stable, mono- or multi-cyclic heterocyclic ring system that comprises carbon atoms and at least one heteroatom selected from the group consisting of N, O, and S, and wherein the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In certain embodiments, the heterocycle is a heteroaryl.

Examples of non-aromatic heterocycles include monocyclic groups such as aziridine, oxirane, thiirane, azetidine, oxetane, thietane, pyrrolidine, pyrroline, imidazoline, pyrazolidine, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin and hexamethyleneoxide.

Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

Examples of polycyclic heterocycles include indolyl (such as, but not limited to, 3-, 4-, 5-, 6- and 7-indolyl), indolinyl, quinolyl, tetrahydroquinolyl, isoquinolyl (such as, but not limited to, 1- and 5-isoquinolyl), 1,2,3,4-tetrahydroisoquinolyl, cinnolinyl, quinoxalinyl (such as, but not limited to, 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (such as, but not limited to, 3-, 4-, 5-, 6- and 7-benzofuryl), 2,3-dihydrobenzofuryl, 1,2-benzisoxazolyl, benzothienyl (such as, but not limited to, 3-, 4-, 5-, 6-, and 7-benzothienyl), benzoxazolyl, benzothiazolyl (such as, but not limited to, 2-benzothiazolyl and 5-benzothiazolyl), purinyl, benzimidazolyl, benztriazolyl, thioxanthinyl, carbazolyl, carbolinyl, acridinyl, pyrrolizidinyl, and quinolizidinyl.

The aforementioned listing of heterocyclyl and heteroaryl moieties is intended to be representative and not limiting.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable" refers to a material, such as a carrier or diluent, which does not abrogate the biological activity or properties of the compound useful within the invention, and is relatively non-toxic, i.e., the material may be administered to a subject without causing undesirable biological effects or interacting in a deleterious manner with any of the components of the composition in which it is contained.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the subject such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the subject. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate;

powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the subject. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, PA), which is incorporated herein by reference.

As used herein, the language "pharmaceutically acceptable salt" refers to a salt of the administered compound prepared from pharmaceutically acceptable non-toxic acids and/or bases, including inorganic acids, inorganic bases, organic acids, organic bases, solvates (including hydrates) and clathrates thereof.

As used herein, a "pharmaceutically effective amount," "therapeutically effective amount" or "effective amount" of a compound is that amount of compound that is sufficient to provide a beneficial effect to the subject to which the compound is administered.

The term "prevent," "preventing" or "prevention" as used herein means avoiding or delaying the onset of symptoms associated with a disease or condition in a subject that has not developed such symptoms at the time the administering of an agent or compound commences.

Disease, condition and disorder are used interchangeably herein.

As used herein, the term "RT" refers to retention time. By the term "specifically bind" or "specifically binds" as used herein is meant that a first molecule preferentially binds to a second molecule (e.g., a particular receptor or enzyme), but does not necessarily bind only to that second molecule.

As used herein, the terms "subject" and "individual" and "patient" can be used interchangeably and may refer to a human or non-human mammal or a bird. Non-human mammals include, for example livestock and pets, such as ovine, bovine, porcine, canine, feline and murine mammals. In certain embodiments, the subject is human.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined elsewhere herein, substituted by one, two or three substituents independently selected from the group consisting of halogen, —OH, alkoxy, tetrahydro-2-H-pyranyl, —$NH_2$, —NH($C_1$-$C_6$ alkyl), —N($C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C≡N, —C(=O)$NH_2$, —C(=O)NH($C_1$-$C_6$)alkyl, —C(=O)N($C_1$-$C_6$)alkyl)$_2$, —$SO_2NH_2$, —$SO_2$NH($C_1$-$C_6$ alkyl), —$SO_2$N($C_1$-$C_6$ alkyl)$_2$, —C(=NH)$NH_2$, and —$NO_2$, in certain embodiments containing one or two substituents independently selected from halogen, —OH, alkoxy, —$NH_2$, trifluoromethyl, —N($CH_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

For aryl, aryl-($C_1$-$C_3$)alkyl and heterocyclyl groups, the term "substituted" as applied to the rings of these groups refers to any level of substitution, namely mono-, di-, tri-, tetra-, or penta-substitution, where such substitution is permitted. The substituents are independently selected, and substitution may be at any chemically accessible position. In certain embodiments, the substituents vary in number between one and four. In other embodiments, the substituents vary in number between one and three. In yet another embodiments, the substituents vary in number between one and two. In yet other embodiments, the substituents are independently selected from the group consisting of $C_1$-$C_6$ alkyl, —OH, $C_1$-$C_6$ alkoxy, halo, amino, acetamido and nitro. As used herein, where a substituent is an alkyl or alkoxy group, the carbon chain may be branched, straight or cyclic.

Unless otherwise noted, when two substituents are taken together to form a ring having a specified number of ring atoms (e.g., $R^2$ and $R^3$ taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given elsewhere herein for "alkyl" and "aryl" respectively.

In certain embodiments, substituents of compounds are disclosed in groups or in ranges. It is specifically intended that the description include each and every individual sub-combination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$0_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl.

The terms "treat," "treating" and "treatment," as used herein, means reducing the frequency or severity with which symptoms of a disease or condition are experienced by a subject by virtue of administering an agent or compound to the subject.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual and partial numbers within that range, for example, 1, 2, 2.7, 3, 4, 5, 5.3, and 6. This applies regardless of the breadth of the range. Compounds The invention includes a compound of formula (I), or a salt, solvate, geometric isomer, any mixture of one or more geometric isomers, stereoisomer (such as, in a non-limiting example, an enantiomer or diastereoisomer thereof), any mixture of one or more stereoisomers (such as, in a non-limiting example, mixtures in any proportion of enantiomers thereof, and/or mixtures in any proportion of diastereoisomers thereof), tautomer, and/or any mixture of tautomers thereof:

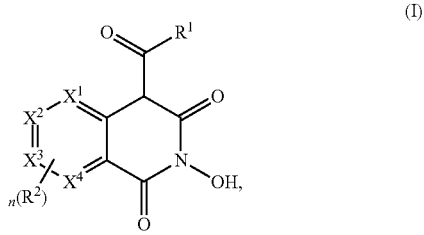

(I)

wherein:
- $R^1$ is selected from the group consisting of —OR' and —NR'R', wherein each occurrence of R' is independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted benzyl, optionally substituted aryl, and optionally substituted heteroaryl;
- each of $X^1$, $X^2$, $X^3$, and $X^4$ is independently selected from the group consisting of N and $CR^3$, with the proviso that 1-2 of $X^1$, $X^2$, $X^3$, and $X^4$ are N;
- $R^2$ and $R^3$ are independently selected from the group consisting of H, $C_1$-$C_6$ alkyl, $C_1$-$C_6$ haloalkyl, $C_1$-$C_6$ haloalkoxy, halo, —CN, —OR", —NR"R", —N($C_0$-$C_6$ alkyl)C(=O)R", —N($C_0$-$C_6$ alkyl)S(=O)$_2$R", —NO$_2$, —S(=O)$_2$NR"R", —OC(=O)R", and —C(=O)O—$C_1$-$C_6$ alkyl, wherein each occurrence of R" is independently selected from the group consisting of H, optionally substituted $C_1$-$C_6$ alkyl, optionally substituted $C_3$-$C_8$ cycloalkyl, and optionally substituted phenyl; and
- n is 0, 1, 2, 3, or 4.

In certain embodiments, each occurrence of alkyl, alkenyl, alkynyl, or cycloalkyl is independently optionally substituted with at least one substituent selected from the group consisting of $C_1$-$C_6$ alkyl, halo, keto (C=O), —OR, optionally substituted phenyl (thus yielding, in non-limiting examples, —($C_1$-$C_3$ alkyl)-(optionally substituted phenyl), such as, but not limited to, benzyl or substituted benzyl), optionally substituted heteroaryl, optionally substituted heterocyclyl, —N(R)(R), —N(R)—(C=O)R, —C(=O)R, —C(=O)(optionally substituted phenyl), —C(=O)(optionally substituted heteroaryl), —C(=O)N(R)(R), —C(=O)(CH$_2$)$_{0-3}$OR, —S(=O)$_2$R, and —SO$_2$N(R)(R), wherein each occurrence of R is independently selected from the group consisting of H, $C_1$-$C_6$ alkyl, and $C_3$-$C_8$ cycloalkyl.

In certain embodiments, each occurrence of aryl (such as phenyl) or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R)(R), —NO$_2$, —S(=O)$_2$N(R)(R), acyl, and $C_1$-$C_6$ alkoxycarbonyl, wherein each occurrence of R is independently selected from the group consisting of H, $C_1$-$C_6$ alkyl, and $C_3$-$C_8$ cycloalkyl.

In certain embodiments, each occurrence of aryl (such as phenyl) or heteroaryl is independently optionally substituted with at least one substituent selected from the group consisting of $C_1$-$C_6$ alkyl, $C_1$-$C_6$ haloalkyl, $C_1$-$C_6$ haloalkoxy, halo, —CN, —OR, —N(R)(R), and $C_1$-$C_6$ alkoxycarbonyl, wherein each occurrence of R is independently selected from the group consisting of H, $C_1$-$C_6$ alkyl, and $C_3$-$C_8$ cycloalkyl.

The invention contemplates any of the compounds disclosed herein, or a salt, solvate, stereoisomer (such as, in a non-limiting example, an enantiomer or diastereoisomer thereof), any mixture of one or more stereoisomers (such as, in a non-limiting example, mixtures in any proportion of enantiomers thereof, and/or mixtures in any proportion of diastereoisomers thereof), tautomer, and/or any mixture of tautomers thereof.

In certain embodiments, the compound is at least one selected from the group consisting of:

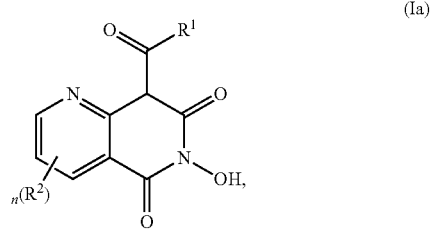

(Ia)

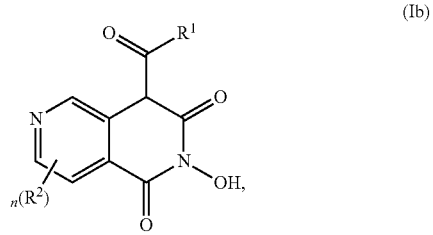

(Ib)

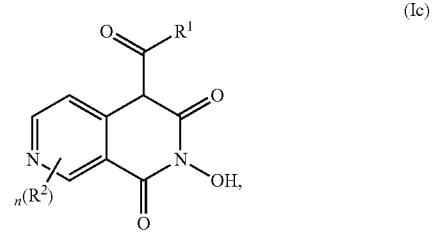

(Ic)

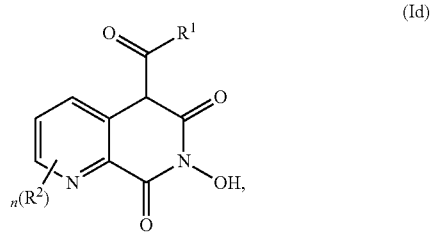

(Id)

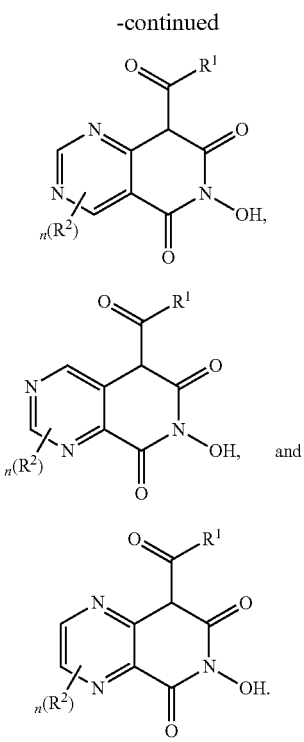

In certain embodiments, the compound is at least one selected form the group consisting of: Ethyl 6-hydroxy-2-methoxy-5,7-dioxo-5,6,7,8-tetrahydro-1,6-naphthyridine-8-carboxylate; N,N-diethyl-6-hydroxy-2-methoxy-5,7-dioxo-5,6,7,8-tetrahydro-1,6-naphthyridine-8-carboxamide; N-(4-chlorophenyl)-6-hydroxy-2-methoxy-5,7-dioxo-5,6,7,8-tetrahydro-1,6-naphthyridine-8-carboxamide; N-(4-fluorophenyl)-6-hydroxy-2-methoxy-5,7-dioxo-5,6,7,8-tetrahydro-1,6-naphthyridine-8-carboxamide; N-(4-Chlorobenzyl)-6-dihydroxy-2-methoxy-5,7-dioxo-5,6,7,8-tetrahydro-1,6-naphthyridine-8-carboxamide; N-(4-fluorobenzyl)-2,6-dihydroxy-5,7-dioxo-5,6,7,8-tetrahydro-1,6-naphthyridine-8-carboxamide; N-(4-Methoxybenzyl)-2,6-dihydroxy-5,7-dioxo-5,6,7,8-tetrahydro-1,6-naphthyridine-8-carboxamide; or a salt, solvate, geometric isomer, stereoisomer, tautomer, or any mixtures thereof.

In certain embodiments, the compound is at least one selected from Table 1, or a salt, solvate, geometric isomer, stereoisomer, any mixture of one or more stereoisomers, tautomer, and/or any mixture of tautomers thereof, as recited herein.

The compounds of the invention may possess one or more stereocenters, and each stereocenter may exist independently in either the (R) or (5) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereoisomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (or pamoic), methanesulfonic, ethanesulfonic, benzenesulfonic, pantothenic, sulfanilic, 2-hydroxyethanesulfonic, trifluoromethanesulfonic, p-toluenesulfonic, cyclohexylaminosulfonic, stearic, alginic, β-hydroxybutyric, salicylic, galactaric, galacturonic acid, glycerophosphonic acids and saccharin (e.g., saccharinate, saccharate). Salts may be comprised of a fraction of one, one or more than one molar equivalent of acid or base with respect to any compound of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (or N-methylglucamine) and procaine. All of these salts may be prepared from the corresponding compound by reacting, for example, the appropriate acid or base with the compound.

Combination Therapies

In one aspect, the compounds of the invention are useful within the methods of the invention in combination with one or more additional agents useful for treating HBV infections. These additional agents may comprise compounds or compositions identified herein, or compounds (e.g., commercially available compounds) known to treat, prevent, or reduce the symptoms of HBV infections.

Non-limiting examples of one or more additional agents useful for treating HBV infections include: (a) reverse transcriptase inhibitors; (b) capsid inhibitors; (c) cccDNA formation inhibitors; (d) sAg secretion inhibitors; (e) oligomeric nucleotides targeted to the Hepatitis B genome; and (f) immunostimulators.

(a) Reverse Transcriptase Inhibitors

In certain embodiments, the reverse transcriptase inhibitor is a reverse-transcriptase inhibitor (NARTI or NRTI). In other embodiments, the reverse transcriptase inhibitor is a nucleotide analog reverse-transcriptase inhibitor (NtARTI or NtRTI).

Reported reverse transcriptase inhibitors include, but are not limited to, entecavir, clevudine, telbivudine, lamivudine, adefovir, and tenofovir, tenofovir disoproxil, tenofovir alafenamide, adefovir dipovoxil, (1R,2R,3R,5R)-3-(6-amino-9H-9-purinyl)-2-fluoro-5-(hydroxymethyl)-4-methylenecyclopentan-1-ol (described in U.S. Pat. No. 8,816,074, incorporated herein in its entirety by reference), emtricitabine, abacavir, elvucitabine, ganciclovir, lobucavir, famciclovir, penciclovir, and amdoxovir.

Reported reverse transcriptase inhibitors further include, but are not limited to, entecavir, lamivudine, and (1R,2R,3R,5R)-3-(6-amino-9H-9-purinyl)-2-fluoro-5-(hydroxymethyl)-4-methylenecyclopentan-1-ol.

Reported reverse transcriptase inhibitors further include, but are not limited to, a covalently bound phosphoramidate or phosphonamidate moiety of the above-mentioned reverse transcriptase inhibitors, or as described in for example U.S. Pat. No. 8,816,074, US Patent Application Publications No. US 2011/0245484 A1, and US 2008/0286230A1, all of which incorporated herein in their entireties by reference.

Reported reverse transcriptase inhibitors further include, but are not limited to, nucleotide analogs that comprise a phosphoramidate moiety, such as, for example, methyl (((((1R,3R,4R,5R)-3-(6-amino-9H-purin-9-yl)-4-fluoro-5-hydroxy-2-methylenecyclopentyl)methoxy)(phenoxy) phosphoryl)-(D or L)-alaninate and methyl (((((1R,2R,3R,4R)-3-fluoro-2-hydroxy-5-methylene-4-(6-oxo-1,6-dihydro-9H-purin-9-yl)cyclopentyl)methoxy)(phenoxy) phosphoryl)-(D or L)-alaninate. Also included are the individual diastereomers thereof, which include, for example, methyl ((R)-(((1R,3R,4R,5R)-3-(6-amino-9H-purin-9-yl)-4-fluoro-5-hydroxy-2-methylenecyclopentyl)methoxy)(phenoxy) phosphoryl)-(D or L)-alaninate and methyl ((S)-(((1R,3R,4R,5R)-3-(6-amino-9H-purin-9-yl)-4-fluoro-5-hydroxy-2-methylenecyclopentyl) methoxy)(phenoxy)phosphoryl)-(D or L)-alaninate.

Reported reverse transcriptase inhibitors further include, but are not limited to, compounds comprising a phosphonamidate moiety, such as, for example, tenofovir alafenamide, as well as those described in U.S. Patent Application Publication No. US 2008/0286230 A1, incorporated herein in its entirety by reference. Methods for preparing stereoselective phosphoramidate or phosphonamidate containing actives are described in, for example, U.S. Pat. No. 8,816,074, as well as U.S. Patent Application Publications No. US 2011/0245484 A1 and US 2008/0286230 A1, all of which incorporated herein in their entireties by reference.

(b) Capsid Inhibitors

As described herein, the term "capsid inhibitor" includes compounds that are capable of inhibiting the expression and/or function of a capsid protein either directly or indirectly. For example, a capsid inhibitor may include, but is not limited to, any compound that inhibits capsid assembly, induces formation of non-capsid polymers, promotes excess capsid assembly or misdirected capsid assembly, affects capsid stabilization, and/or inhibits encapsidation of RNA (pgRNA). Capsid inhibitors also include any compound that inhibits capsid function in a downstream event(s) within the replication process (e.g., viral DNA synthesis, transport of relaxed circular DNA (rcDNA) into the nucleus, covalently closed circular DNA (cccDNA) formation, virus maturation, budding and/or release, and the like). For example, in certain embodiments, the inhibitor detectably inhibits the expression level or biological activity of the capsid protein as measured, e.g., using an assay described herein. In certain embodiments, the inhibitor inhibits the level of rcDNA and downstream products of viral life cycle by at least 5%, at least 10%, at least 20%, at least 50%, at least 75%, or at least 90%.

Reported capsid inhibitors include, but are not limited to, compounds described in International Patent Applications Publication Nos WO 2013006394, WO 2014106019, and WO2014089296, all of which incorporated herein in their entireties by reference.

Reported capsid inhibitors also include, but are not limited to, the following compounds and pharmaceutically acceptable salts and/or solvates thereof: Bay-41-4109 (see Int'l Patent Application Publication No. WO 2013144129), AT-61 (see Int'l Patent Application Publication No. WO 1998033501; and King, et al., 1998, Antimicrob. Agents Chemother. 42(12):3179-3186), DVR-01 and DVR-23 (see Int'l Patent Application Publication No. WO 2013006394, and Campagna, et al., 2013, J. Virol. 87(12):6931, all of which incorporated herein in their entireties by reference.

In addition, reported capsid inhibitors include, but are not limited to, those generally and specifically described in U.S. Patent Application Publication Nos. US 2015/0225355, US 2015/0132258, US 2016/0083383, US 2016/0052921 and Int'l Patent Application Publication Nos. WO 2013096744, WO 2014165128, WO 2014033170, WO 2014033167, WO 2014033176, WO 2014131847, WO 2014161888, WO 2014184350, WO 2014184365, WO 2015059212, WO 2015011281, WO 2015118057, WO 2015109130, WO 2015073774, WO 2015180631, WO 2015138895, WO 2016089990, WO 2017015451, WO 2016183266, WO 2017011552, WO 2017048950, WO2017048954, WO 2017048962, WO 2017064156 and are incorporated herein in their entirety by reference.

(c) cccDNA Formation Inhibitors

Covalently closed circular DNA (cccDNA) is generated in the cell nucleus from viral rcDNA and serves as the transcription template for viral mRNAs. As described herein, the term "cccDNA formation inhibitor" includes compounds that are capable of inhibiting the formation and/or stability of cccDNA either directly or indirectly. For example, a cccDNA formation inhibitor may include, but is not limited to, any compound that inhibits capsid disassembly, rcDNA entry into the nucleus, and/or the conversion of rcDNA into cccDNA. For example, in certain embodiments, the inhibitor detectably inhibits the formation and/or stability of the cccDNA as measured, e.g., using an assay described herein. In certain embodiments, the inhibitor inhibits the formation and/or stability of cccDNA by at least 5%, at least 10%, at least 20%, at least 50%, at least 75%, or at least 90%.

Reported cccDNA formation inhibitors include, but are not limited to, compounds described in Int'l Patent Application Publication No. WO 2013130703, and are incorporated herein in their entirety by reference.

In addition, reported cccDNA formation inhibitors include, but are not limited to, those generally and specifically described in U.S. Patent Application Publication No. US 2015/0038515 A1, and are incorporated herein in their entirety by reference.

(d) sAg Secretion Inhibitors

As described herein, the term "sAg secretion inhibitor" includes compounds that are capable of inhibiting, either directly or indirectly, the secretion of sAg (S, M and/or L surface antigens) bearing subviral particles and/or DNA containing viral particles from HBV-infected cells. For example, in certain embodiments, the inhibitor detectably inhibits the secretion of sAg as measured, e.g., using assays known in the art or described herein, e.g., ELISA assay or by Western Blot. In certain embodiments, the inhibitor inhibits the secretion of sAg by at least 5%, at least 10%, at least 20%, at least 50%, at least 75%, or at least 90%. In certain embodiments, the inhibitor reduces serum levels of sAg in a patient by at least 5%, at least 10%, at least 20%, at least 50%, at least 75%, or at least 90%.

Reported sAg secretion inhibitors include compounds described in U.S. Pat. No. 8,921,381, as well as compounds described in U.S. Patent Application Publication Nos. US 2015/0087659 and US 2013/0303552, all of which are incorporated herein in their entireties by reference.

In addition, reported sAg secretion inhibitors include, but are not limited to, those generally and specifically described in Int'l Patent Application Publication Nos. WO 2015113990, WO 2015173164, US 2016/0122344, WO 2016107832, WO 2016023877, WO 2016128335, WO 2016177655, WO 2016071215, WO 2017013046, WO 2017016921, WO 2017016960, WO 2017017042, WO 2017017043, WO 2017102648, WO 2017108630, WO 2017114812, WO 2017140821 and are incorporated herein in their entirety by reference.

(e) Immunostimulators

The term "immunostimulator" includes compounds that are capable of modulating an immune response (e.g., stimulate an immune response (e.g., an adjuvant)). Immunostimulators include, but are not limited to, polyinosinic:polycytidylic acid (poly I:C) and interferons.

Reported immunostimulators include, but are not limited to, agonists of stimulator of IFN genes (STING) and interleukins. Reported immunostimulators further include, but are not limited to, HBsAg release inhibitors, TLR-7 agonists (such as, but not limited to, GS-9620, RG-7795), T-cell stimulators (such as, but not limited to, GS-4774), RIG-1 inhibitors (such as, but not limited to, SB-9200), and SMAC-mimetics (such as, but not limited to, Birinapant).

(f) Oligomeric Nucleotides

Reported oligomeric nucleotides targeted to the Hepatitis B genome include, but are not limited to, Arrowhead-ARC-520 (see U.S. Pat. No. 8,809,293; and Wooddell et al., 2013, Molecular Therapy 21(5):973-985, all of which incorporated herein in their entireties by reference).

In certain embodiments, the oligomeric nucleotides can be designed to target one or more genes and/or transcripts of the HBV genome. Oligomeric nucleotide targeted to the Hepatitis B genome also include, but are not limited to, isolated, double stranded, siRNA molecules, that each include a sense strand and an antisense strand that is hybridized to the sense strand. In certain embodiments, the siRNA target one or more genes and/or transcripts of the HBV genome.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Synthesis

The present invention further provides methods of preparing the compounds of the present invention. Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

It is appreciated that where typical or preferred process conditions (i.e., reaction temperatures, times, mole ratios of reactants, solvents, pressures, and so forth) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high performance liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene, et al., Protective Groups in Organic Synthesis, 2d. Ed. (Wiley & Sons, 1991), the entire disclosure of which is incorporated by reference herein for all purposes.

The reactions or the processes described herein can be carried out in suitable solvents that can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

A compound of formula (I) can be prepared, for example, according to the synthetic methods outlined in Scheme I. It should be noted that the absolute stereochemistry of the chiral center(s) represented in Scheme I is merely illustrative, and these Schemes may be used to prepare any of the stereoisomers (or any mixtures thereof) of any of the compounds of the invention.

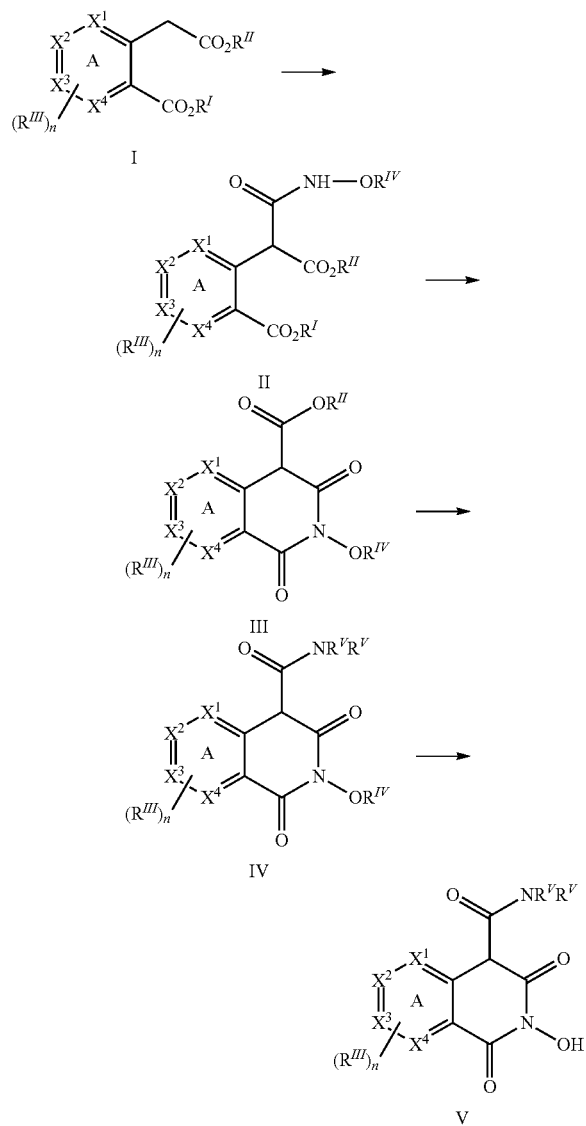

Scheme I.

In a non-limiting example, compound I (wherein each occurrence of $R^{III}$ is independently selected, and wherein 1-2 groups from $X^1$-$X^4$ are N, so as to generate a heteroaryl ring A) can be converted to an intermediate that comprises an activated carbonyl group at the benzylic position (for example, by treatment with 1,1-carbonyldiimidazole in the presence of base), which then can be reacted with an O-protected hydroxylamine to yield compound II. Cyclization of compound II under basic conditions affords compound III, which can then be reacted with an amine (wherein each occurrence of $R^V$ is independently selected) to yield compound IV. Removal of $R^{IV}$ in compound IV affords compound V.

Methods

The invention provides a method of treating or preventing hepatitis virus infection in a subject. In certain embodiments, the infection comprises hepatitis B virus (HBV) infection. In other embodiments, the method comprises administering to the subject in need thereof a therapeutically effective amount of at least one compound of the invention. In yet other embodiments, the compound of the invention is the only antiviral agent administered to the subject. In yet other embodiments, the at least one compound is administered to the subject in a pharmaceutically acceptable composition. In yet other embodiments, the subject is further administered at least one additional agent useful for treating the hepatitis infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the subject is co-administered the at least one compound and the at least one additional agent. In yet other embodiments, the at least one compound and the at least one additional agent are coformulated.

The invention further provides a method of inhibiting RNAse H activity in a HBV. In certain embodiments, the method comprises contacting the HBV with at least one compound of the invention. In other embodiments, the HBV is infecting a subject. In yet other embodiments, the subject is administered a therapeutically effective amount of at least one compound of the invention. In yet other embodiments, the at least one compound is administered to the subject in a pharmaceutically acceptable composition. In yet other embodiments, the compound of the invention is the only antiviral agent administered to the subject. In yet other embodiments, the subject is further administered at least one additional agent useful for treating HBV infection. In yet other embodiments, the at least one additional agent comprises at least one selected from the group consisting of reverse transcriptase inhibitor; capsid inhibitor; cccDNA formation inhibitor; sAg secretion inhibitor; oligomeric nucleotide targeted to the Hepatitis B genome; and immunostimulator. In yet other embodiments, the subject is co-administered the at least one compound and the at least one additional agent. In yet other embodiments, the at least one compound and the at least one additional agent are coformulated.

The invention further provides a method of screening compounds for activity against HBV, as exemplified herein. In certain embodiments, the method comprises a HepDE19 assay with bDNA quantitation of HBV rcDNA. HepDE19 cell culture system is a HepG2 (human hepatocarcinoma) derived cell line that supports HBV DNA replication and cccDNA formation in a tetracycline (Tet)-regulated manner and produces HBV rcDNA and a detectable reporter molecule dependent on the production and maintenance of cccDNA (Tavis & Lomonosova, 2015, Antiviral Res. 118:

132-138). In certain non-limiting embodiments, HepDE19 (50,000 cells/well) are plated in 96 well collagen-coated tissue-culture treated microtiter plates in DMEM/F12 medium supplemented with 10% fetal bovine serum, 1% penicillin-streptomycin and 1 µg/ml tetracycline and incubated in a humidified incubator at 37° C. and 5% $CO_2$ overnight. Next day, the cells are switched to fresh medium without tetracycline and incubated for 4 hrs at 37° C. and 5% $CO_2$. The cells are treated with fresh Tet-free medium with compounds at concentrations starting at 25 µM and a serial, ½ log, 8-point, titration series in duplicate. The final DMSO concentration in the assay is 0.5%. The plates are incubated for 7 days in a humidified incubator at 37° C. and 5% $CO_2$. Following a 7 day-incubation, the level of rcDNA present in the inhibitor-treated wells is measured using a Quantigene 2.0 bDNA assay kit (Affymetrix, Santa Clara, Calif.) with HBV specific custom probe set and manufacturer's instructions.

In order to differentiate HBV RNaseH inhibitors from other classes of HBV inhibitors (such as, for example, nucleos(t)ide analogs or capsid inhibitors), the assay method is configured by incorporating the quantitation of both the minus-strand and the plus-strand of HBV rcDNA levels using specifically designed HBV probe sets. This is based on the observation that inhibition of RNaseH enzyme activity results in a block of the synthesis of the plus strand synthesis by the viral polymerase that follows the synthesis of the minus-strand of rcDNA (Guo, et al., 2007, J. Virol. 81:12472-12484). In this system, an RNaseH inhibitor thus shows inhibition of the plus-strand formation but minimal effect on the synthesis of the minus strand of rcDNA. In contrast, treatment with HBV inhibitors such as a nucleos (t)ide analogs or capsid inhibitors reduces production of both strands of HBV rcDNA in cells. Concurrently, the effect of compounds on cell viability can be assessed using replicate plates, plated at a density of 5,000 cells/well and incubated for 4 days, to determine the ATP content as a measure of cell viability using the cell-titer glo reagent (CTG; Promega Corporation, Madison, Wis.) as per manufacturer's instructions. The plates are read using a Victor luminescence plate reader (PerkinElmer Model 1420 Multilabel counter), and the relative luminescence units (RLU) data generated from each well was calculated as % inhibition of the untreated control wells and analyzed using XL-Fit module in Microsoft Excel to determine $EC_{50}$ and $EC_{90}$ (bDNA) and $CC_{50}$ (CTG) values using a 4-parameter curve fitting algorithm.

In certain embodiments, the subject is a mammal. In other embodiments, the mammal is a human.

Pharmaceutical Compositions and Formulations

The invention provides pharmaceutical compositions comprising at least one compound of the invention or a salt or solvate thereof, which are useful to practice methods of the invention. Such a pharmaceutical composition may consist of at least one compound of the invention or a salt or solvate thereof, in a form suitable for administration to a subject, or the pharmaceutical composition may comprise at least one compound of the invention or a salt or solvate thereof, and one or more pharmaceutically acceptable carriers, one or more additional ingredients, or some combination of these. At least one compound of the invention may be present in the pharmaceutical composition in the form of a physiologically acceptable salt, such as in combination with a physiologically acceptable cation or anion, as is well known in the art.

In certain embodiments, the pharmaceutical compositions useful for practicing the method of the invention may be administered to deliver a dose of between 1 ng/kg/day and 100 mg/kg/day. In other embodiments, the pharmaceutical compositions useful for practicing the invention may be administered to deliver a dose of between 1 ng/kg/day and 1,000 mg/kg/day.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

Pharmaceutical compositions that are useful in the methods of the invention may be suitably developed for nasal, inhalational, oral, rectal, vaginal, pleural, peritoneal, parenteral, topical, transdermal, pulmonary, intranasal, buccal, ophthalmic, epidural, intrathecal, intravenous or another route of administration. A composition useful within the methods of the invention may be directly administered to the brain, the brainstem, or any other part of the central nervous system of a mammal or bird. Other contemplated formulations include projected nanoparticles, microspheres, liposomal preparations, coated particles, polymer conjugates, resealed erythrocytes containing the active ingredient, and immunologically-based formulations.

In certain embodiments, the compositions of the invention are part of a pharmaceutical matrix, which allows for manipulation of insoluble materials and improvement of the bioavailability thereof, development of controlled or sustained release products, and generation of homogeneous compositions. By way of example, a pharmaceutical matrix may be prepared using hot melt extrusion, solid solutions, solid dispersions, size reduction technologies, molecular complexes (e.g., cyclodextrins, and others), microparticulate, and particle and formulation coating processes. Amorphous or crystalline phases may be used in such processes.

The route(s) of administration will be readily apparent to the skilled artisan and will depend upon any number of factors including the type and severity of the disease being treated, the type and age of the veterinary or human patient being treated, and the like.

The formulations of the pharmaceutical compositions described herein may be prepared by any method known or hereafter developed in the art of pharmacology and pharmaceutics. In general, such preparatory methods include the step of bringing the active ingredient into association with a carrier or one or more other accessory ingredients, and then, if necessary or desirable, shaping or packaging the product into a desired single-dose or multi-dose unit.

As used herein, a "unit dose" is a discrete amount of the pharmaceutical composition comprising a predetermined amount of the active ingredient. The amount of the active ingredient is generally equal to the dosage of the active ingredient that would be administered to a subject or a convenient fraction of such a dosage such as, for example, one-half or one-third of such a dosage. The unit dosage form may be for a single daily dose or one of multiple daily doses (e.g., about 1 to 4 or more times per day). When multiple daily doses are used, the unit dosage form may be the same or different for each dose.

Although the descriptions of pharmaceutical compositions provided herein are principally directed to pharmaceutical compositions suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, the compositions of the invention are formulated using one or more pharmaceutically acceptable excipients or carriers. In certain embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol, recombinant human albumin (e.g., RECOMBU-MIN®), solubilized gelatins (e.g., GELOFUSINE®), and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), recombinant human albumin, solubilized gelatins, suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, isotonic agents, for example, sugars, sodium chloride, or polyalcohols such as mannitol and sorbitol, are included in the composition. Prolonged absorption of the injectable compositions may be brought about by including in the composition an agent that delays absorption, for example, aluminum monostearate or gelatin.

Formulations may be employed in admixtures with conventional excipients, i.e., pharmaceutically acceptable organic or inorganic carrier substances suitable for oral, parenteral, nasal, inhalational, intravenous, subcutaneous, transdermal enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or fragrance-conferring substances and the like. They may also be combined where desired with other active agents, e.g., other analgesic, anxiolytics or hypnotic agents. As used herein, "additional ingredients" include, but are not limited to, one or more ingredients that may be used as a pharmaceutical carrier.

The composition of the invention may comprise a preservative from about 0.005% to 2.0% by total weight of the composition. The preservative is used to prevent spoilage in the case of exposure to contaminants in the environment. Examples of preservatives useful in accordance with the invention include but are not limited to those selected from the group consisting of benzyl alcohol, sorbic acid, parabens, imidurea and combinations thereof. One such preservative is a combination of about 0.5% to 2.0% benzyl alcohol and 0.05% to 0.5% sorbic acid.

The composition may include an antioxidant and a chelating agent which inhibit the degradation of the compound. Antioxidants for some compounds are BHT, BHA, alpha-tocopherol and ascorbic acid in the exemplary range of about 0.01% to 0.3%, or BHT in the range of 0.03% to 0.1% by weight by total weight of the composition. The chelating agent may be present in an amount of from 0.01% to 0.5% by weight by total weight of the composition. Exemplary chelating agents include edetate salts (e.g. disodium edetate) and citric acid in the weight range of about 0.01% to 0.20%, or in the range of 0.02% to 0.10% by weight by total weight of the composition. The chelating agent is useful for chelating metal ions in the composition that may be detrimental to the shelf life of the formulation. While BHT and disodium edetate are exemplary antioxidant and chelating agent, respectively, for some compounds, other suitable and equivalent antioxidants and chelating agents may be substituted therefore as would be known to those skilled in the art.

Liquid suspensions may be prepared using conventional methods to achieve suspension of the active ingredient in an aqueous or oily vehicle. Aqueous vehicles include, for example, water, and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethyl cellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g., polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin, acacia, and ionic or non ionic surfactants. Known preservatives include, but are not limited to, methyl, ethyl, or n-propyl para-hydroxybenzoates, ascorbic acid, and sorbic acid. Known sweetening agents include, for example, glycerol, propylene glycol, sorbitol, sucrose, and saccharin.

Liquid solutions of the active ingredient in aqueous or oily solvents may be prepared in substantially the same manner as liquid suspensions, the primary difference being that the active ingredient is dissolved, rather than suspended in the solvent. As used herein, an "oily" liquid is one which comprises a carbon-containing liquid molecule and which exhibits a less polar character than water. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water, and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, ionic and non-ionic surfactants, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e., such as with a physiologically degradable material), and methods of absorbing an aqueous or oily solution or suspension into an absorbent material, with or without subsequent drying. Methods for mixing components include physical milling, the use of pellets in solid and suspension formulations and mixing in a transdermal patch, as known to those skilled in the art.

Administration/Dosing

The regimen of administration may affect what constitutes an effective amount. The therapeutic formulations may be administered to the patient either prior to or after the onset of a disease or disorder. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, such as a human, may be carried out using known procedures, at dosages and for periods of time effective to treat a disease or disorder contemplated herein. An effective amount of the therapeutic compound necessary to achieve a therapeutic effect may vary according to factors such as the activity of the particular compound employed; the time of administration; the rate of excretion of the compound; the duration of the treatment; other drugs, compounds or materials used in combination with the compound; the state of the disease or disorder, age, sex, weight, condition, general health and prior medical history of the patient being treated, and like factors well-known in the medical arts. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 0.01 mg/kg to 100 mg/kg of body weight/per day. One of ordinary skill in the art would be able to study the relevant factors and make the determination regarding the effective amount of the therapeutic compound without undue experimentation.

The compound may be administered to an animal as frequently as several times daily, or it may be administered less frequently, such as once a day, once a week, once every two weeks, once a month, or even less frequently, such as once every several months or even once a year or less. It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on. The frequency of the dose is readily apparent to the skilled artisan and depends upon a number of factors, such as, but not limited to, type and severity of the disease being treated, and type and age of the animal.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder in a patient.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It will be readily apparent to one skilled in the art that the frequency of administration of the various combination compositions of the invention will vary from subject to subject depending on many factors including, but not limited to, age, disease or disorder to be treated, gender, overall health, and other factors. Thus, the invention should not be construed to be limited to any particular dosage regime and the precise dosage and composition to be administered to any patient will be determined by the attending physician taking all other factors about the patient into account.

Compounds of the invention for administration may be in the range of from about 1 μg to about 7,500 mg, about 20 μg to about 7,000 mg, about 40 μg to about 6,500 mg, about 80 μg to about 6,000 mg, about 100 μg to about 5,500 mg, about 200 μg to about 5,000 mg, about 400 μg to about 4,000 mg, about 800 μg to about 3,000 mg, about 1 mg to about 2,500 mg, about 2 mg to about 2,000 mg, about 5 mg to about 1,000 mg, about 10 mg to about 750 mg, about 20 mg to about 600 mg, about 30 mg to about 500 mg, about 40 mg to about 400 mg, about 50 mg to about 300 mg, about 60 mg to about 250 mg, about 70 mg to about 200 mg, about 80 mg to about 150 mg, and any and all whole or partial increments there-in-between.

In some embodiments, the dose of a compound of the invention is from about 0.5 μg and about 5,000 mg. In some embodiments, a dose of a compound of the invention used in compositions described herein is less than about 5,000 mg, or less than about 4,000 mg, or less than about 3,000 mg, or less than about 2,000 mg, or less than about 1,000 mg, or less than about 800 mg, or less than about 600 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder in a patient.

The term "container" includes any receptacle for holding the pharmaceutical composition or for managing stability or water uptake. For example, in certain embodiments, the container is the packaging that contains the pharmaceutical composition, such as liquid (solution and suspension), semi-solid, lyophilized solid, solution and powder or lyophilized formulation present in dual chambers. In other embodiments, the container is not the packaging that contains the pharmaceutical composition, i.e., the container is a receptacle, such as a box or vial that contains the packaged pharmaceutical composition or unpackaged pharmaceutical composition and the instructions for use of the pharmaceutical composition. Moreover, packaging techniques are well known in the art. It should be understood that the instructions for use of the pharmaceutical composition may be contained on the packaging containing the pharmaceutical composition, and as such the instructions form an increased functional relationship to the packaged product. However, it should be understood that the instructions may contain information pertaining to the compound's ability to perform its intended function, e.g., treating, preventing, or reducing a disease or disorder in a patient.

Administration

Routes of administration of any of the compositions of the invention include inhalational, oral, nasal, rectal, parenteral, sublingual, transdermal, transmucosal (e.g., sublingual, lingual, (trans)buccal, (trans)urethral, vaginal (e.g., trans- and perivaginally), (intra)nasal, and (trans)rectal), intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, emulsions, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral application, particularly suitable are tablets, dragees, liquids, drops, capsules, caplets and gelcaps. Other formulations suitable for oral administration include, but are not limited to, a powdered or granular formulation, an aqueous or oily suspension, an aqueous or oily solution, a paste, a gel, toothpaste, a mouthwash, a coating, an oral rinse, or an emulsion. The compositions intended for oral use may be prepared according to any method known in the art and such compositions may contain one or more agents selected from the group consisting of inert, non-toxic, generally recognized as safe (GRAS) pharmaceutically excipients which are suitable for the manufacture of tablets. Such excipients include, for example an inert diluent such as lactose; granulating and disintegrating agents such as cornstarch; binding agents such as starch; and lubricating agents such as magnesium stearate.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically controlled release tablets. Tablets may further comprise a sweetening agent, a flavoring agent, a coloring agent, a preservative, or some combination of these in order to provide for pharmaceutically elegant and palatable preparation. Hard capsules comprising the active ingredient may be made using a physiologically degradable composition, such as gelatin. The capsules comprise the active ingredient, and may further comprise additional ingredients including, for example, an inert solid diluent such as calcium carbonate, calcium phosphate, or kaolin.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin from animal-derived collagen or from a hypromellose, a modified form of cellulose, and manufactured using optional mixtures of gelatin, water and plasticizers such as sorbitol or glycerol. Such soft capsules comprise the active ingredient, which may be mixed with water or an oil medium such as peanut oil, liquid paraffin, or olive oil.

For oral administration, the compounds of the invention may be in the form of tablets or capsules prepared by conventional means with pharmaceutically acceptable excipients such as binding agents; fillers; lubricants; disintegrates; or wetting agents. If desired, the tablets may be coated using suitable methods and coating materials such as OPADRY® film coating systems available from Colorcon, West Point, Pa. (e.g., OPADRY® OY Type, OYC Type, Organic Enteric OY-P Type, Aqueous Enteric OY-A Type, OY-PM Type and OPADRY® White, 32K18400). It is understood that similar type of film coating or polymeric products from other companies may be used.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface-active agents include, but are not limited to, sodium lauryl sulfate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multi-layer tablet comprising a layer providing for the delayed release of one or more compounds useful within the methods of the invention, and a further layer providing for the immediate release of one or more compounds useful within the methods of the invention. Using a wax/pH-sensitive polymer mix, a gastric insoluble composition may be obtained in which the active ingredient is entrapped, ensuring its delayed release.

Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl para-hydroxy benzoates or sorbic acid). Liquid formulations of a pharmaceutical composition of the invention which are suitable for oral administration may be prepared, packaged, and sold either in liquid form or in the form of a dry product intended for reconstitution with water or another suitable vehicle prior to use.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Injectable formulations may also be prepared, packaged, or sold in devices such as patient-controlled analgesia (PCA) devices. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form in a recombinant human albumin, a fluidized gelatin, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance which is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Topically administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

Enhancers of permeation may be used. These materials increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

One acceptable vehicle for topical delivery of some of the compositions of the invention may contain liposomes. The composition of the liposomes and their use are known in the art (i.e., U.S. Pat. No. 6,323,219).

In alternative embodiments, the topically active pharmaceutical composition may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein "amount effective" shall mean an amount sufficient to cover the region of skin surface where a change is desired. An active compound should be present in the amount of from about 0.0001% to about 15% by weight volume of the composition. For example, it should be present in an amount from about 0.0005% to about 5% of the composition; for example, it should be present in an amount of from about 0.001% to about 1% of the composition. Such compounds may be synthetically-or naturally derived.

Buccal Administration

A pharmaceutical composition of the invention may be prepared, packaged, or sold in a formulation suitable for buccal administration. Such formulations may, for example, be in the form of tablets or lozenges made using conventional methods, and may contain, for example, 0.1 to 20% (w/w) of the active ingredient, the balance comprising an orally dissolvable or degradable composition and, optionally, one or more of the additional ingredients described herein. Alternately, formulations suitable for buccal administration may comprise a powder or an aerosolized or atomized solution or suspension comprising the active ingredient. Such powdered, aerosolized, or aerosolized formulations, when dispersed, may have an average particle or droplet size in the range from about 0.1 to about 200 nanometers, and may further comprise one or more of the additional ingredients described herein. The examples of formulations described herein are not exhaustive and it is understood that the invention includes additional modifications of these and other formulations not described herein, but which are known to those of skill in the art.

Rectal Administration

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e., about 20° C.) and which is liquid at the rectal temperature of the subject (i.e., about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants, and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants, and preservatives.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 20030147952, 20030104062, 20030104053, 20030044466, 20030039688, and 20020051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the compositions and/or formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range. The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials & Methods

The following procedures can be utilized in evaluating and selecting compounds that inhibit hepatitis B virus infection.

Analytical Methods:

(a) LCMS Methods

LCMS Method A: Waters Acquity UPLC system employing a Waters Acquity UPLC BEH C18, 1.7 um, 50×2.1 mm column with an aqueous acetonitrile based solvent gradient of 2-98% $CH_3CN/H_2O$ (0.05% TFA) over 1.5 mins. Flow rate=0.8 mL/min.

LCMS Method B: Waters Acquity UPLC system employing a Waters Acquity UPLC BEH C18, 1.7 um, 50×2.1 mm column with an aqueous acetonitrile based solvent gradient of 2-98% $CH_3CN/H_2O$ (0.05% TFA) over 1.0 mins. Flow rate=0.8 mL/min.

LCMS Method C: Waters Acquity UPLC H class with Waters SQD 2 MS employing a Waters Acquity UPLC BEH C18, 1.7 μm, (50×2.1 mm) column with an aqueous component of 0.1% Formic acid in water and an organic component of 0.1% formic acid in acetonitrile. Solvent events: 0-0.3 min, Isocratic 3% (0.1% formic acid/acetonitrile); 0.3 min-2.2 min, Linear gradient of 3-98% (0.1% formic acid/acetonitrile); 2.2 min-3.2 min, Isocratic 98% (0.1% formic acid/acetonitrile); 3.2 min-4.5 min, Isocratic 98% (0.1% formic acid/acetonitrile). Flow rate=0.6 mL/min.

LCMS Method D: Waters Acquity UPLC system employing a Waters Acquity UPLC BEH C18 (50 mm×2.1 mm, 1.7 um); Mobile Phase: A—0.05% formic acid in water; B—0.05% formic acid in acetonitrile; time (min)/ %B: 0/3, 0.4/3, 2/98, 3.4/98, 3.5/3, 4/3; Column Temp: 35° C.; Flow Rate: 0.6 ml/min.

(b) HPLC Methods

HPLC Method A: Shimadzu 20AB system employing a Luna C18, 5 u, 50×2 mm column with an aqueous component of 0.075% TFA in water and an organic component of 0.0375% TFA in acetonitrile. Solvent events: 0.01 min -4 min, Linear gradient of 10-80% of (0.0375% TFA in acetonitrile); 4 min-4.9 min, isocratic 80% of (0.0375% TFA in acetonitrile); 4.9 min-4.92 min, Linear gradient of 80-10% of (0.0375% TFA in acetonitrile); 4.9 min-5.50 min, Isocratic 10% of (0.0375% TFA in acetonitrile). Flow rate=1 mL/min.

HPLC Method B: Waters alliance 2695/2996 system employing a)(Bridge C18 (4.6×150 mm) 3.5 um. Mobile Phase A: Acetonitrile; B: 0.1% FA in water, Gradient (T %/A): 0/5, 1.5/5, 3/15, 7/55, 10/95, 16/100, 18/5,20/5. Flow Rate: 1.0 mL per min. Temperature: Ambient. Diluent: $CH_3CN:H_2O$ (70:30) +DMSO).

Assay Protocols:

(a) AlphaLisa eAg.

Evaluation of anti-HBV activity of the compounds in in vitro cell culture studies was conducted using a modification of the assay system described in Cai et al., 2012, Antimicrobial Agents Chemotherapy 56(8):4277-88 and PCT/EP/2015/06838. In the DESHAe82 cell culture system, the HA epitope-tagged secreted HBV "e antigen" (HBeAg) and HBV precore RNA are produced only from the cccDNA circular template that is formed after HBV replication in absence of Tetracycline (Tet). The DESHAe82 cell line produces high levels of cccDNA synthesis and HA-HBeAg, and high specific readout signals with low noise. Two assay systems, a chemiluminescence ELISA (CLIA) and a proximity scintillation assay (AlphaLISA) were developed and used for high-sensitivity detection of HA-tagged HBeAg.

To test the compound, DESHAe82 were plated in 96 well tissue-culture treated microtiter plates in DMEM/F12 medium supplemented with 10% fetal bovine serum+1% penicillin-streptomycin with Tet, and incubated in a humidified incubator at 37° C. and 5% $CO_2$ overnight. Next day, the cells were switched to fresh medium without Tet and treated with a test compound, over a range of concentrations (compound was solubilized in 100% DMSO before dilution in cell culture media, and the final DMSO concentration in the assay was 0.5%), and incubated for a duration of 9 days in a humidified incubator at 37° C. and 5% $CO_2$. Untreated negative control samples (0.5% DMSO only) were included on each plate in multiple wells. On day 9, media was harvested and removed to a fresh plate, and level of HA-HBeAg was determined by CLIA or AlphaLISA. Anti-cccDNA activity of each test compound concentration was calculated as a percentage of HA-HBeAg signal detected in negative control samples versus compound-treated samples, and $EC_{50}$ value for each compound was defined as the concentration that reduced the HA-HBeAg signal by 50%.

(b) HepDE19 Assay with bDNA Quantitation of HBV rcDNA.

HepDE19 cell culture system is a HepG2 (human hepatocarcinoma) derived cell line that supports HBV DNA replication and cccDNA formation in a tetracycline (Tet)-regulated manner and produces HBV rcDNA and a detectable reporter molecule dependent on the production and maintenance of cccDNA (Guo, et al., 2007, J. Virol. 81:12472-12484). HepDE19 (50,000 cells/well) were plated in 96 well collagen-coated tissue-culture treated microtiter plates in DMEM/F12 medium supplemented with 10% fetal bovine serum, 1% penicillin-streptomycin and 1μg/ml tetracycline and incubated in a humidified incubator at 37° C. and 5% $CO_2$ overnight. Next day, the cells were switched to fresh medium without tetracycline and incubated for 4 hrs at 37° C. and 5%$CO_2$. The cells were treated with fresh Tet-free medium with compounds at concentrations starting at 25 μM and a serial, ½ log, 8-point, titration series in duplicate. The final DMSO concentration in the assay was 0.5%. The plates were incubated for 7 days in a humidified incubator at 37° C. and 5% $CO_2$. Following a 7 day-incubation, the level of rcDNA present in the inhibitor-treated wells was measured using a Quantigene 2.0 bDNA assay kit (Affymetrix, Santa Clara, Calif.) with HBV specific custom probe set and manufacturer's instructions. In order to differentiate HBV RNaseH inhibitors from other classes of HBV inhibitors (such as, for example, nucleos(t)ide analogs or capsid inhibitors), the assay method was configured by incorporating the quantitation of both the minus-strand and the plus-strand of HBV rcDNA levels using specifically designed HBV probe sets. This is based on the observation that inhibition of RNaseH enzyme activity results in a block of the synthesis of the plus strand synthesis by the viral polymerase that follows the synthesis of the minus-strand of rcDNA (Tavis & Lomonosova, 2015, Antiviral Res. 118:132-138). In this system, an RNaseH inhibitor thus shows prominent inhibition of the plus-strand formation but minimal effect on the synthesis of the minus strand of rcDNA. In contrast, treatment with HBV inhibitors such as a nucleos(t)ide analogs or capsid inhibitors reduces production of both strands of HBV rcDNA in cells. Concurrently, the effect of compounds on cell viability was assessed using replicate plates, plated at a density of 5,000 cells/well and incubated for 4 days, to determine the ATP content as a measure of cell viability using the cell-titer glo reagent (CTG; Promega Corporation, Madison, Wis.) as per manufacturer's instructions. The plates were read using a Victor luminescence plate reader (PerkinElmer Model 1420 Multilabel counter), and the relative luminescence units (RLU) data generated from each well was calculated as % inhibition of the untreated control wells and analyzed using XL-Fit module in Microsoft Excel to determine $EC_{50}$ and $EC_{90}$ (bDNA) and $CC_{50}$ (CTG) values using a 4-parameter curve fitting algorithm.

EXAMPLE 1

Synthesis of Compounds 1-7

Scheme II.

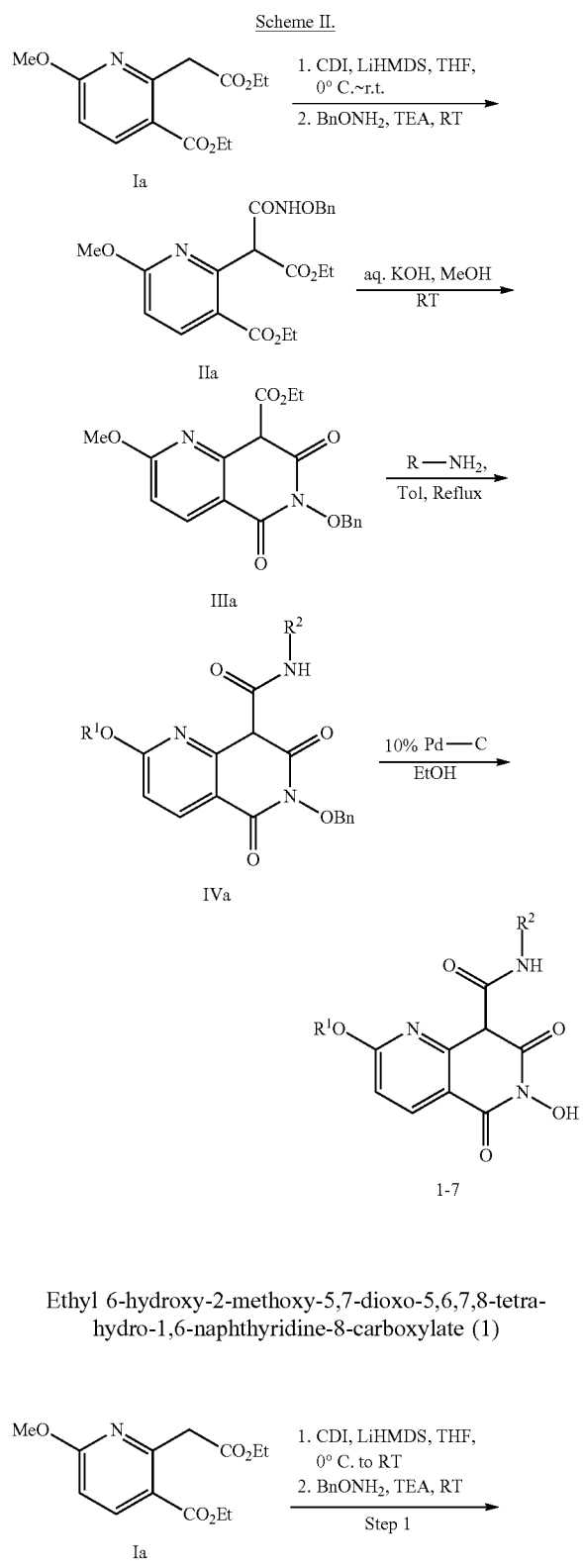

Ethyl 6-hydroxy-2-methoxy-5,7-dioxo-5,6,7,8-tetra-hydro-1,6-naphthyridine-8-carboxylate (1)

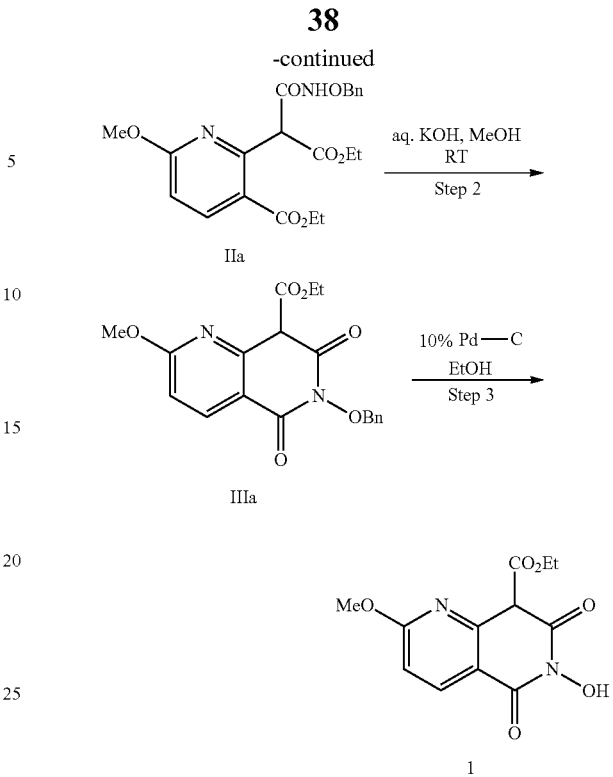

Step 1: Ethyl 2-(1-((benzyloxy)amino)-3-ethoxy-1,3-dioxopropan-2-yl)-6-methoxynicotinate (IIa)

To a solution of Ia (synthesized by the protocols described in WO2009/079768 A1) (10 g, 37.4 mmol) in THF (100 mL) was added LiHMDS (1 M, 74.8 mL) at 0° C. for 0.5 hours. After that, CDI (12.1 g, 74.82 mmol) was added, and the mixture was stirred at 12° C. for 14.5 hours. To the reaction mixture were added TEA (22.7 g, 225 mmol) and BnONH$_2$ (18.4 g, 149.7 mmol), and the mixture was stirred at 12° C. for 15 hours. The reaction mixture was added to saturated aqueous NH$_4$Cl solution (400 mL) and extracted with ethyl acetate (3×1 L). The combined organic layers were washed with brine (2×400 mL), dried over anhydrous Na$_2$SO$_4$, filtered and concentrated under reduced pressure to give a residue. The residue was purified by flash column chromatography (SiO$_2$, 0-10% MeOH in dichloromethane). Compound IIa (16.0 g, 38.4 mmol, 51.4% yield) was obtained as colorless oil. LCMS: m/z: 417 [M+H]$^+$ observed (Method A), RT=0.85 min. $^1$H NMR: (CDCl$_3$, 400 MHz): δ 8.21 (d, J=8.8 Hz, 1H), 7.36-7.26 (m, 5H), 6.71 (d, J=8.8 Hz, 1H), 5.67 (s, 1H), 5.28-5.25 (m, 3H), 4.29-4.22 (m, 4H), 3.82 (s, 3H), 1.34-1.22 (m, 6H).

Step 2: Ethyl 6-(benzyloxy)-2-methoxy-5,7-dioxo-5,6,7,8-tetrahydro-1,6-naphthyridine-8-carboxylate (IIIa)

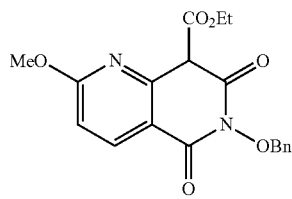 [SMILES: CCOC(=O)C1C(=O)N(OCc2ccccc2)C(=O)c2ccc(OC)nc21]

To a solution of IIa (16 g, 38.3 mmol) in MeOH (200 mL) was added KOH (4.3 g, 76.7 mmol) in H₂O (200 mL). The mixture was stirred at 12° C. for 15 hours. The reaction mixture was extracted with ethyl acetate (3×1 L), and the combined organic layers were washed with brine (2×1 L), dried over anhydrous Na₂SO₄, filtered and concentrated under reduced pressure to give a residue. The residue was triturated with ethyl acetate (500 mL) to give compound Ma (6.71 g, 47% yield) as a white solid. LCMS: m/z: 371 [M+H]⁺ observed (Method A), RT: 0.76 min. HPLC (Method A) RT=2.33 min. ¹H NMR (DMSO-d₆, 400 MHz): δ 8.57 (d, J=8.4 Hz, 1H), 7.60-7.57 (m, 2H), 7.44-7.38 (m, 3H), 6.80 (d, J=8.4 Hz, 1H), 4.99 (s, 2H), 4.31-4.25 (m, 3H), 4.17 (s, 3H), 1.32-1.28 (m, 3H).

Step 3: Ethyl 6-hydroxy-2-methoxy-5,7-dioxo-5,6,7,8-tetrahydro-1,6-naphthyridine-8-carboxylate (1)

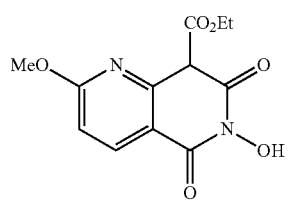 [SMILES: CCOC(=O)C1C(=O)N(O)C(=O)c2ccc(OC)nc21]

To a stirred solution of IIIa (110 mg, 0.3 mmol) in methanol (10 mL) was added 10% Pd—C (50% wet, 0.15 mg), and the system was stirred under H₂ atmosphere (balloon) at room temperature for 3 h. The reaction mixture was filtered through a pad of Celite and evaporated to dryness. The obtained crude compound was purified by preparative HPLC method (Column: Inertsil ODS-3, 5.0 μm. Pump A: 0.1% Formic Acid, Pump B: 0-90% Acetonitrile, Flow rate: 18.00 ml/min. UV detector: 215 nm and 254 nm) to provide 1 (30 mg, 26%) as a yellow solid. LCMS: m/z 281.20 [M+H]⁺ observed (Method B). ¹H NMR (CDCl₃, 300 MHz): δ 8.78 (d, J=8.4 Hz, 1H), 6.50 (d, J=8.4 Hz, 1H), 4.48-4.41 (m, 2H), 4.19 (s, 3H), 4.15 (s, 1H), 1.48-1.43 (m, 3H).

N,N-diethyl-6-hydroxy-2-methoxy-5,7-dioxo-5,6,7,8-tetrahydro-1,6-naphthyridine-8-carboxamide (2)

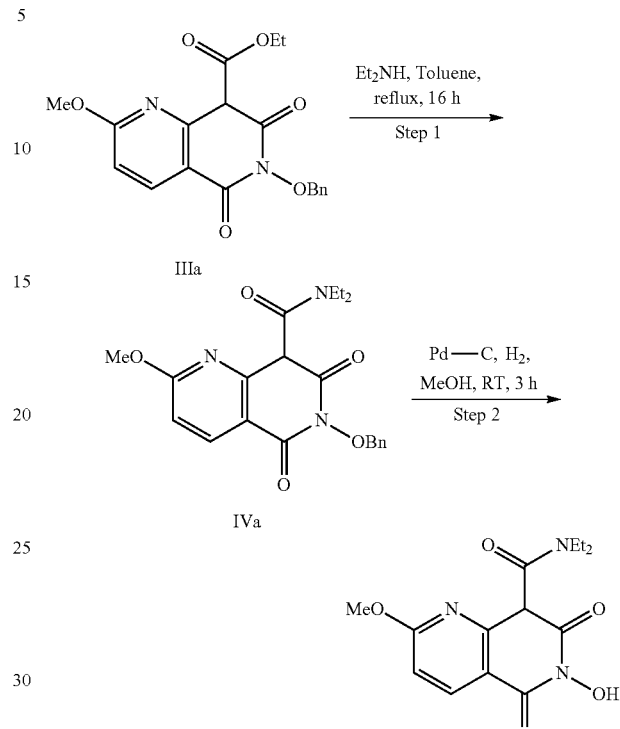

Step 1: 6-(Benzyloxy)-N,N-diethyl-2-methoxy-5,7-dioxo-5,6,7,8-tetrahydro-1,6-naphthyridine-8-carboxamide (IVa)

To a stirred solution of IIIa (0.3g, 0.81 mmol) in toluene (10 mL) was added N,N-diethylamine (0.177 g, 2.43 mmol), and the system was heated at reflux for 16 h. The reaction mixture was cooled to room temperature, quenched with water (10 mL) and extracted with EtOAc (2×10 mL). The combined organics were dried over Na₂SO₄, filtered, was evaporated to dryness. The obtained crude compound was purified by flash silica gel column chromatography (0-80% EtOAc-petroleum ether) to provide IVa (150 mg, 56%) as a white gum. LCMS: m/z 397.83 [M+H]⁺ observed; (Method C) RT=1.82 min.

Step 2: N,N-diethyl-6-hydroxy-2-methoxy-5,7-dioxo-5,6,7,8-tetrahydro-1,6-naphthyridine-8-carboxamide (2)

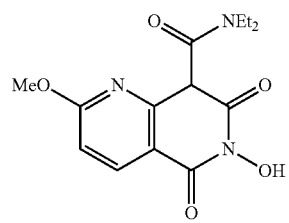

To a stirred solution of IVa (150 mg, 0.377 mmol) in methanol (10 mL) was added 10% Pd—C (50% wet, 0.15 mg) and the system was stirred under H$_2$ atmosphere (balloon) at room temperature for 3 h. The reaction mixture was filtered through a pad of Celite and evaporated to dryness. The obtained crude compound was purified by preparative HPLC to provide 2 (30 mg, 26% yield) as a yellow solid. LCMS: m/z 308.37 [M+H]$^+$ observed (Method C), RT=1.68 min. HPLC (Method B): RT 6.95 min (97%). $^1$H NMR (400 MHz, DMSO-d$_6$): δ 10.60 (s, 1H), 8.24 (d, J=8.4 Hz, 1H), 6.97 (d, J=8.4 Hz, 1H), 3.88-3.80 (m, 7H), 3.42 (m, 1H), 1.04-0.85 (m, 6H).

N-(4-chlorophenyl)-6-hydroxy-2-methoxy-5,7-dioxo-5,6,7,8-tetrahydro-1,6-naphthyridine-8-carboxamide (3)

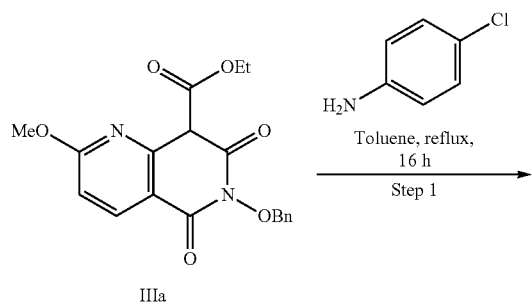

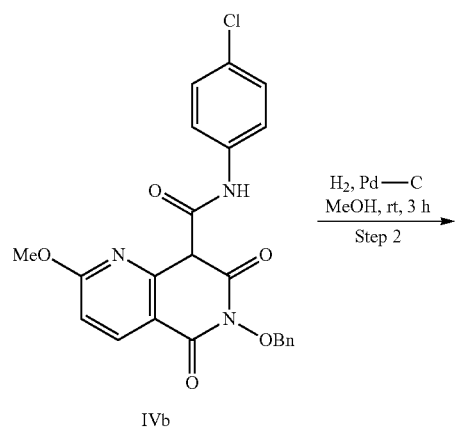

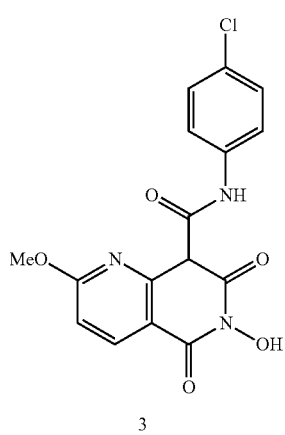

Step 1: 6-(benzyloxy)-N-(4-chlorophenyl)-2-methoxy-5,7-dioxo-5,6,7,8-tetrahydro-1,6-naphthyridine-8-carboxamide (IVb)

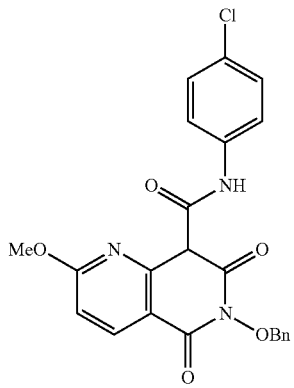 [SMILES: COc1ccc2c(n1)C(C(=O)Nc1ccc(Cl)cc1)C(=O)N(OCc1ccccc1)C2=O]

To a stirred solution of IIIa (0.4 g, 1.081 mmol) in toluene (10 mL) was added 4-chloro aniline (0.41 g, 3.24 mmol) and the reaction mixture was heated to reflux for 16 h. The reaction mixture was cooled to room temperature, quenched with water (10 mL) and extracted with EtOAc (2×10 mL). The combined organics layers were dried over Na$_2$SO$_4$, filtered, and evaporated to dryness. The crude product was purified by flash silica gel column chromatography (0-60% EtOAc in petroleum ether) to afford IVb (180 mg, 47%) as an off-white solid. LCMS: m/z 452.13 [M+H]$^+$ observed (Method C), RT=2.6 min. $^1$H NMR (400 MHz, DMSO-d$_6$): δ 8.60 (d, J=8.4 Hz, 1H), 7.72-7.60 (m, 4H) 7.42-7.10 (m, 5H), 6.87 (d, J=8.4 Hz, 1H), 5.10 (s, 2H), 4.20 (s, 3H) and 2.63-2.61 (m, 1H).

Step 2: N-(4-chlorophenyl)-6-hydroxy-2-methoxy-5,7-dioxo-5,6,7,8-tetrahydro-1,6-naphthyridine-8-carboxamide (3)

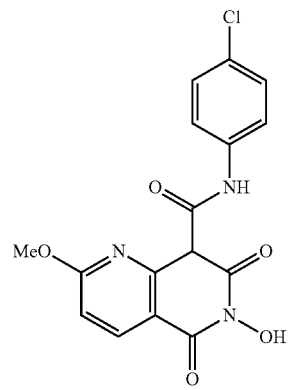 [SMILES: COc1ccc2c(n1)C(C(=O)Nc1ccc(Cl)cc1)C(=O)N(O)C2=O]

To a stirred solution of IVb (180 mg, 0.399 mmol) in methanol-DMF(1:1, 10 mL) was added 10% Pd—C (50% wet, 18 mg) and the reaction mixture was stirred under H$_2$ atmosphere (balloon) at room temperature for 3 h. The reaction mixture was filtered through a pad of Celite and evaporated to dryness. The obtained crude compound was purified by preparative HPLC to provide 6 (21 mg, 20% yield) as a yellow solid. LCMS: m/z 362.06 [M+H]$^+$ observed (Method C), RT=2.08 min. HPLC (Method B): 97.13%, RT=5.93 min. $^1$H NMR (400 MHz, DMSO-d$_6$): δ 12.23 (br s, 1H), 8.61 (d, J=8.4 Hz, 1H), 7.68-7.62 (m, 2H), 7.43-7.35 (m, 2H), 6.86 (d, J=8.4 Hz, 1H) and 4.19 (s, 3H).

N-(4-fluorophenyl)-6-hydroxy-2-methoxy-5,7-di-oxo-5,6,7,8-tetrahydro-1,6-naphthyridine-8-carboxamide (4):

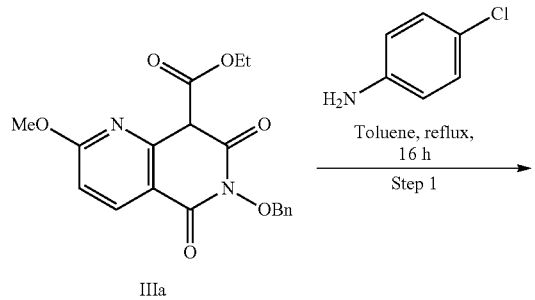

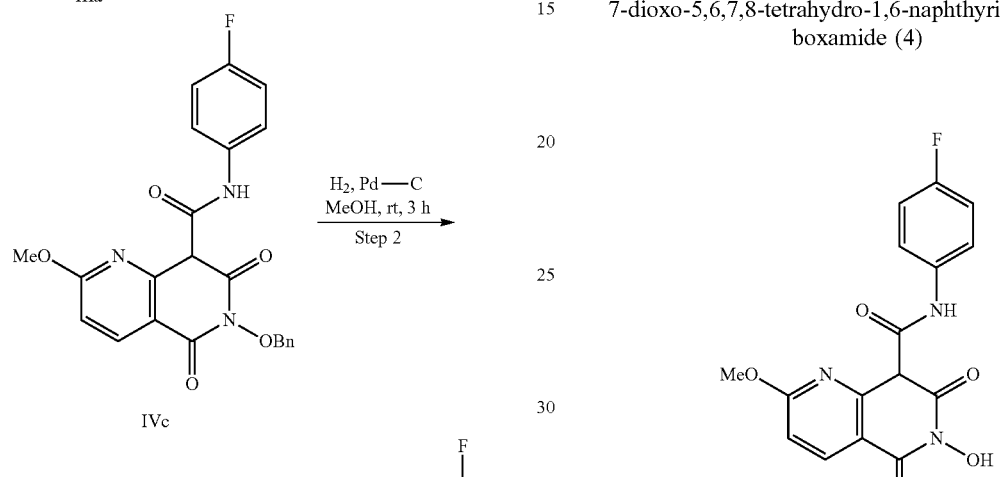

Step 1: 6-(Benzyloxy)-N-(4-fluorophenyl)-2-methoxy-5,7-dioxo-5,6,7,8-tetrahydro-1,6-naphthyridine-8-carboxamide (IVc)

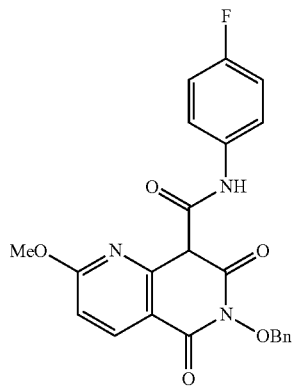 [SMILES: COc1ccc2c(n1)C(C(=O)Nc1ccc(F)cc1)C(=O)N(OCc1ccccc1)C2=O]

To a stirred solution of IIIa (0.3 g, 0.81 mmol) in toluene (10 mL) was added 4-fluoroaniline (0.27g, 2.432 mmol) and the system was heated to reflux for 16 h. The reaction mixture was cooled to room temperature, quenched with water (10 mL) and extracted with EtOAc (2×10 mL). The combined organics were dried over $Na_2SO_4$, filtered, and evaporated to dryness. The obtained crude compound was purified by silica gel column chromatography (0-60% EtOAc in petroleum ether) to provide IVc (130 mg, 36% yield) as a white gum. LCMS: m/z 434.20 [M–H]$^+$ observed (Method-C), RT=2.33 min.

Step 2: N-(4-fluorophenyl)-6-hydroxy-2-methoxy-5,7-dioxo-5,6,7,8-tetrahydro-1,6-naphthyridine-8-carboxamide (4)

To a stirred solution of IVc (130mg, 0.298 mmol) in methanol-DMF(1:1, 10 mL) was added 10% Pd—C (50% wet, 13 mg) and the reaction mixture was stirred under $H_2$ atmosphere (balloon) at room temperature for 3 h. The reaction mixture was filtered through a pad of Celite and evaporated to dryness. The crude compound was purified by preparative HPLC to provide 4 (21 mg, 20%) as a yellow solid. LCMS: m/z 356.05 [M+H]$^+$ observed (Method C), RT=1.67 min. HPLC (Method C): 95.43%, RT=5.42 min. $^1$H NMR (400 MHz, DMSO-$d_6$): δ 12.14 (br s, 1H), 10.43 (br s, 1H), 8.61 (d, J=8.4 Hz, 1H), 7.66-7.64 (m, 2H), 7.25-7.19 (m, 2H), 6.84 (d, J=8.4 Hz, 1H), 4.18 (s, 3H).

N-(4-chlorobenzyl)-6-hydroxy-2-methoxy-5,7-di-oxo-5,6,7,8-tetrahydro-1,6-naphthyridine-8-carboxamide (5)

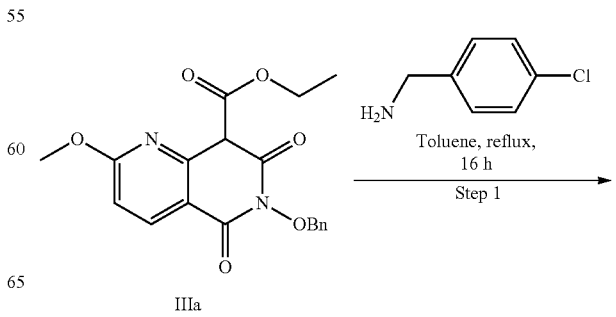

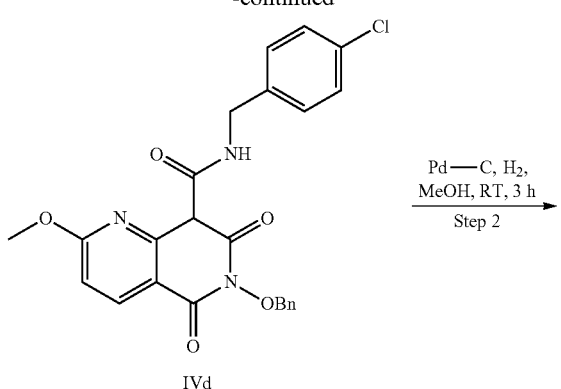

IVd

Step 1: 6-(benzyloxy)-N-(4-chlorobenzyl)-2-methoxy-5,7-dioxo-5,6,7,8-tetrahydro-1,6 naphthyridine-8-carboxamide (IVd)

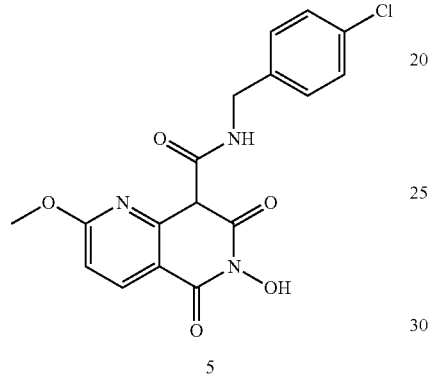

To a stirred solution of IIIa (0.3g, 0.81 mmol) in toluene (10 mL) was added (4-chlorophenyl)methanamine (0.342 g, 2.4 mmol) and the reaction mixture was heated to reflux for 16 h. The reaction mixture was cooled to room temperature, quenched with water (30 mL) and extracted with EtOAc (2×50 mL). The combined organic layers were dried over Na₂SO₄, filtered, and evaporated to dryness. The obtained crude compound was purified by flash silica gel column chromatography (0-80% EtOAc in petroleum ether) to provide IVd (0.130 g, 56% yield) as a yellow gum. LCMS: m/z: 466.10 [M+H]⁺ observed; (Method C) RT=2.51 min.

Step 2: N-(4-chlorobenzyl)-6-hydroxy-2-methoxy-5,7-dioxo-5,6,7,8-tetrahydro-1,6-naphthyridine-8-carboxamide (5)

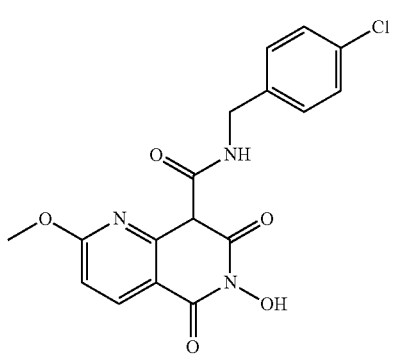 [SMILES: COc1ccc2c(n1)C(C(=O)NCc1ccc(Cl)cc1)C(=O)N(O)C2=O]

To a stirred solution of IVd (50 mg, 0.107 mmol) in methanol (10 mL) was added 10% Pd—C (50% wet, 0.15 mg) and the system was stirred under H₂ atmosphere (balloon) at room temperature for 3 h. The reaction mixture was filtered through a pad of Celite and evaporated to dryness. The obtained crude compound was purified by preparative HPLC to afford 5 (15 mg, 37% yield) as a yellow solid. LCMS: m/z 375.90 [M+H]⁺ observed (Method C), RT=1.81 min. HPLC (Method C): 97.90%, RT=6.23 min. ¹H NMR (400 MHz, DMSO-d₆): δ 8.45 (d, J=8.4 Hz, 1H), 7.41-7.30 (m, 6H), 6.73 (d, J=8.4 Hz, 1H), 4.61 (s, 2H) and 3.28 (s, 3H).

N-(4-fluorobenzyl)-2,6-dihydroxy-5,7-dioxo-5,6,7,8-tetrahydro-1,6-naphthyridine-8-carboxamide (6)

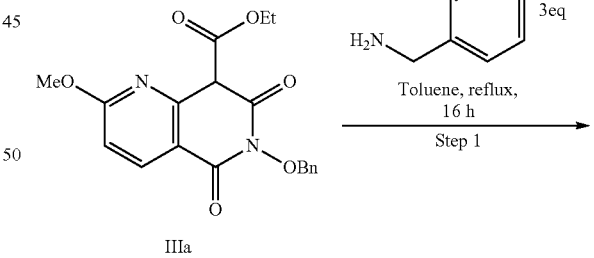

IIIa

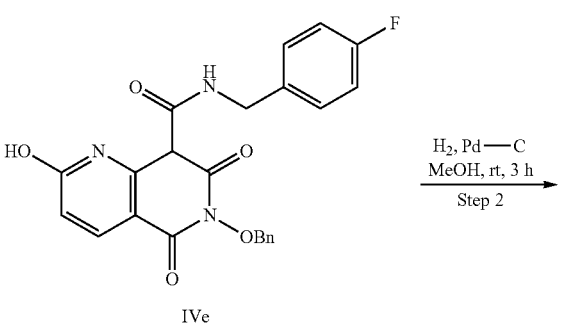

IVe

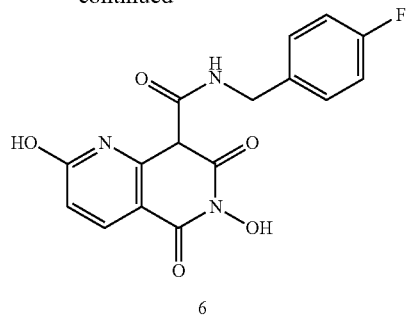

Step 1: N-(4-fluorobenzyl)-2,6-dihydroxy-5,7-dioxo-5,6,7,8-tetrahydro-1,6-naphthyridine-8-carboxamide (IVe)

To a stirred solution of IIIa (0.3 g, 0.81 mmol, 1.0 eq.) in toluene (10 mL) was added 4-fluorobenzylamine (0.304g, 2.43 mmol) and the reaction mixture was heated to reflux for 16 h. The reaction mixture was cooled to room temperature, quenched with water (10 mL) and extracted with EtOAc (2×10 mL). The combined organic layers were dried over $Na_2SO_4$, filtered and evaporated to dryness. The obtained crude compound was purified by silica gel column chromatography (0-80% EtOAc in petroleum ether) to afford IVe (150 mg, 43% yield) as a white gum. LCMS: m/z 436.14 $[M+H]^+$ observed (Method C), RT=1.86 min. $^1H$ NMR (400 MHz, DMSO-$d_6$): δ 12.63 (br s, 1H), 10.39 (br s, 1H), 7.63 (d, J=8.8 Hz, 1H), 7.53-7.15 (m, 9H), 5.75-5.78 (d, J=8.8 Hz, 1H), 4.95 (s, 2H), 4.44 (br s, 2H).

Step 2: N-(4-fluorobenzyl)-2,6-dihydroxy-5,7-dioxo-5,6,7,8-tetrahydro-1,6-naphthyridine-8-carboxamide (6)

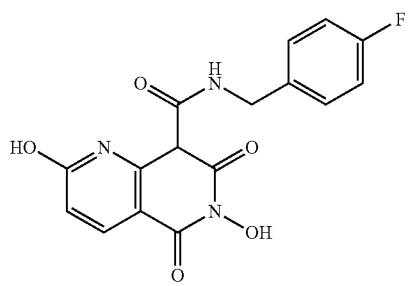 [SMILES: O=C(NCc1ccc(F)cc1)C1C(=O)N(O)C(=O)c2ccc(O)nc21]

To a stirred solution of IVe (150mg, 0.38 mmol) in methanol (10 mL) was added 10% Pd—C (50% wet, 15 mg) and the system was stirred under $H_2$ atmosphere (balloon) at room temperature for 3 h. The reaction mixture was filtered through a pad of Celite and evaporated to dryness. The obtained crude compound was purified by preparative HPLC to give 6 (70 mg, 53% yield) as a pale-yellow solid. LCMS: m/z 346.12 $[M+H]^+$ observed (Method C), RT=1.66 min. HPLC (Method C): 95.00%, RT=4.16 min. $^1H$ NMR (400 MHz, DMSO-$d_6$): δ 13.53 (s, 1H), 10.41 (br s, 1H), 7.69 (d, J=8.8 Hz, 1H), 7.49-7.17 (m, 4H), 5.76 (d, J=8.8 Hz, 1H), 4.45-4.41 (m, 2H).

2,6-Dihydroxy-N-(4-methoxybenzyl)-5,7-dioxo-5,6,7,8-tetrahydro-1,6-naphthyridine-8-carboxamide (7)

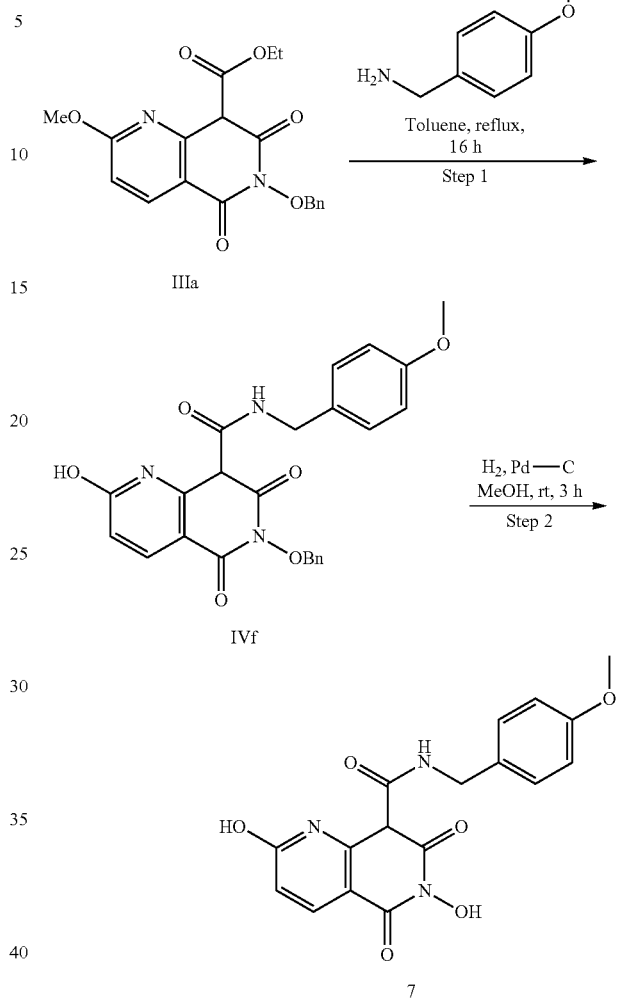

Step 1: 6-(benzyloxy)-2-hydroxy-N-(4-methoxybenzyl)-5,7-dioxo-5,6,7,8-tetrahydro-1,6-naphthyridine-8-carboxamide (IVf)

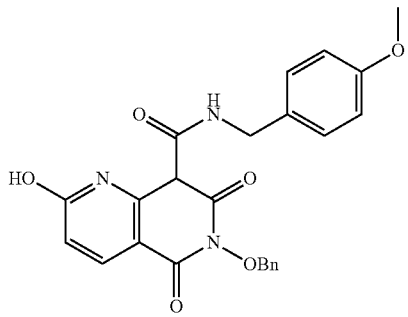

To a stirred solution of IIIa (0.3 g, 0.81 mmol) in toluene (10 mL) was added 4-methoxy benzylamine (0.304 g, 2.43 mmol) and the reaction mixture was heated to reflux for 16 h. The reaction mixture was cooled to room temperature, quenched with water (10 mL) and extracted with EtOAc (2×10 mL). The combined organic layers were dried over $Na_2SO_4$, filtered and evaporated to dryness. The obtained crude compound was purified by flash silica gel column chromatography (0-60% EtOAc in petroleum ether) to afford IVf (160 mg, 44.2% yield) as an off-white gum. LCMS: m/z: 448.20 [M+H]+ observed (Method-C), RT=2.05 min. $^1$H NMR (400 MHz, DMSO-$d_6$): δ 13.79 (s, 1H), 10.29 (s, 1H), 7.78 (d, J=8.0 Hz, 1H) 7.40-7.37 (m, 5H), 7.21-6.90 (m, 3H), 5.78-5.76 (m, 2H), 4.94 (s, 2H), 4.38-4.37 (m, 2H), 3.73-3.71 (m, 4H).

Step 2: 2,6-Dihydroxy-N-(4-methoxybenzyl)-5,7-dioxo-5,6,7,8-tetrahydro-1,6-naphthyridine-8-carboxamide (7)

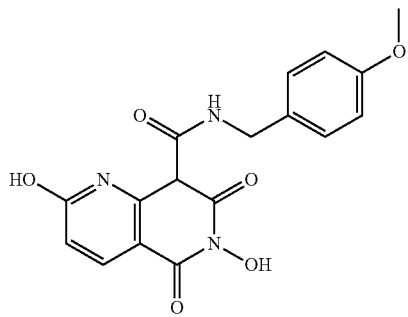

To a stirred solution of IVf (90 mg, 0.2 mmol) in methanol (10 mL) was added 10% Pd—C (50% wet, 16 mg), and the reaction mixture was stirred under $H_2$ atmosphere (balloon) at room temperature for 3 h. The reaction mixture was filtered through a pad of Celite and the solvent evaporated to dryness. The obtained crude compound was purified by preparative HPLC to provide 7 (10 mg, 14% yield) as a gray solid. LCMS: m/z 356.05 [M−H]+ observed (Method C), RT=1.63 min. HPLC (Method C): 94.00%, RT=4.07 min. $^1$H NMR (400 MHz, DMSO-$d_6$+TFA): δ 8.29 (d, J=8.0 Hz, 1H), 7.28 (d, J=8.8 Hz, 2H), 6.92-6.90 (m, 3H), 4.46 (s, 2H), 3.75 (s, 3H).

Example 2

Biological Activity

Biological activity of selected compounds of the invention are summarized in Table 1.

TABLE 1

| # | Structure | Nomenclature | AlphaLisa_eAg $EC_{50}$ (μM) | bDNA_RC DNA $EC_{50}$ (μM) | bDNA_RC DNA PS $EC_{50}$ (μM) |
|---|---|---|---|---|---|
| 1 | 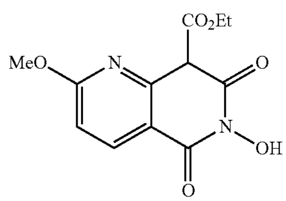 | Ethyl 6-hydroxy-2-methoxy-5,7-dioxo-5,6,7,8-tetrahydro-1,6-naphthyridine-8-carboxylate | 2.4 | >25 | N/A |
| 2 | 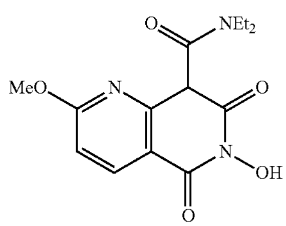 | N,N-diethyl-6-hydroxy-2-methoxy-5,7-dioxo-5,6,7,8-tetrahydro-1,6-naphthyridine-8-carboxamide | 1.5 | >25 | 11.2 |
| 3 | 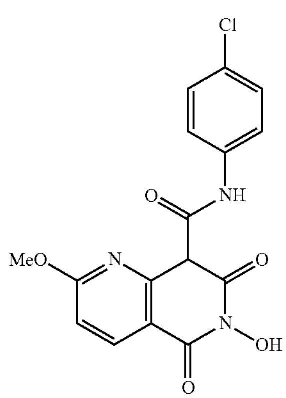 [SMILES: COc1ccc2c(n1)C(C(=O)Nc1ccc(Cl)cc1)C(=O)N(O)C2=O] | N-(4-chlorophenyl)-6-hydroxy-2-methoxy-5,7-dioxo-5,6,7,8-tetrahydro-1,6-naphthyridine-8-carboxamide | 9.6 | 9.4 | 16 |

TABLE 1-continued

| # | Structure | Nomenclature | AlphaLisa_eAg EC$_{50}$ (μM) | bDNA_RC DNA EC$_{50}$ (μM) | bDNA_RC DNA PS EC$_{50}$ (μM) |
|---|---|---|---|---|---|
| 4 | 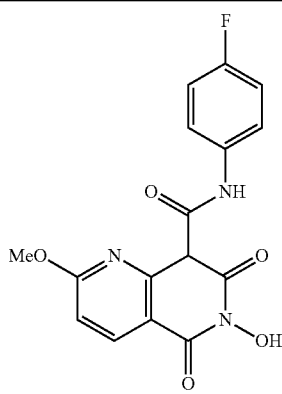 | N-(4-fluorophenyl)-6-hydroxy-2-methoxy-5,7-dioxo-5,6,7,8-tetrahydro-1,6-naphthyridine-8-carboxamide | 9.6 | >25 | N/A |
| 5 | 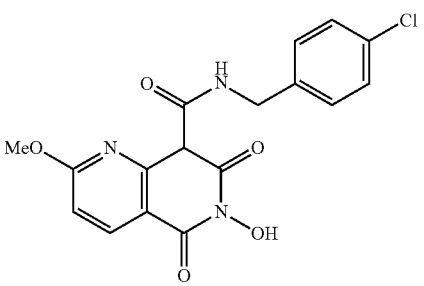 [SMILES: COc1ccc2c(n1)C(C(=O)NCc1ccc(Cl)cc1)C(=O)N(O)C2=O] | N-(4-Chlorobenzyl)-6-dihydroxy-2-methoxy-5,7-dioxo-5,6,7,8-tetrahydro-1,6-naphthyridine-8-carboxamide | >50 | >25 | >25 |
| 6 | 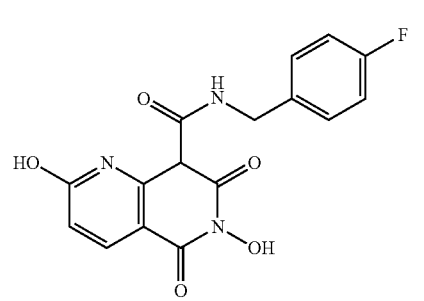 [SMILES: O=C(NCc1ccc(F)cc1)C1C(=O)N(O)C(=O)c2ccc(O)nc21] | N-(4-fluorobenzyl)-2,6-dihydroxy-5,7-dioxo-5,6,7,8-tetrahydro-1,6-naphthyridine-8-carboxamide | 3.6 | >25 | 15.02 |
| 7 | 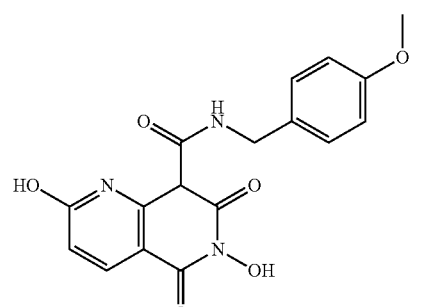 | N-(4-Methoxybenzyl)-2,6-dihydroxy-5,7-dioxo-5,6,7,8-tetrahydro-1,6-naphthyridine-8-carboxamide | N/A | N/A | N/A |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I):

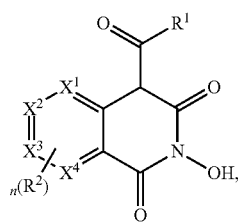

(I)

wherein:
R$^1$ is selected from the group consisting of —OR' and —NR'R', wherein each occurrence of R' is independently selected from the group consisting of H, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, optionally substituted benzyl, optionally substituted aryl, and optionally substituted heteroaryl;
each of X$^1$, X$^2$, X$^3$, and X$^4$ is independently selected from the group consisting of N and CR$^3$, with the proviso that 1-2 of X$^1$, X$^2$, X$^3$, and X$^4$ are N;
each occurrence of R$^2$ and R$^3$ is independently selected from the group consisting of H, C$_1$-C$_6$ alkyl, C$_1$-C$_6$ haloalkyl, C$_1$-C$_6$ haloalkoxy, halo, —CN, —OR", —NR"R", —N(C$_0$-C$_6$ alkyl)C(=O)R", —N(C$_0$-C$_6$ alkyl)S(=O)$_2$R", —NO$_2$, —S(=O)$_2$NR"R", —OC(=O)R", and —C(=O)O—C$_1$-C$_6$ alkyl, wherein each occurrence of R" is independently selected from the group consisting of H, optionally substituted C$_1$-C$_6$ alkyl, optionally substituted C$_3$-C$_8$ cycloalkyl, and optionally substituted phenyl; and
n is 0, 1, 2, 3, or 4;
or a salt, geometric isomer, stereoisomer, tautomer, or any mixtures thereof.

2. The compound of claim 1, wherein each occurrence of alkyl, alkenyl, alkynyl, or cycloalkyl is independently optionally substituted with at least one substituent selected from the group consisting of C$_1$-C$_6$ alkyl, halo, keto (C=O), —OR, optionally substituted phenyl, optionally substituted heteroaryl, optionally substituted heterocyclyl, —N(R)(R), —N(R)—(C=O)R, —C(=O)R, —C(=O)(optionally substituted phenyl), —C(=O)(optionally substituted heteroaryl), —C(=O)N(R)(R), —C(=O)(CH$_2$)$_{0-3}$OR, —S(=O)$_2$R, and —SO$_2$N(R)(R), wherein each occurrence of R is independently selected from the group consisting of H, C$_1$-C$_6$ alkyl, and C$_3$-C$_8$ cycloalkyl.

3. The compound of claim 1, wherein each occurrence of aryl or heteroaryl is independently optionally substituted with at least one substituent selected from the group consisting of C$_1$-C$_6$ alkyl, C$_1$-C$_6$ haloalkyl, C$_1$-C$_6$ haloalkoxy, halo, —CN, —OR, —N(R)(R), —NO$_2$, —S(=O)$_2$N(R)(R), acyl, and C$_1$-C$_6$ alkoxycarbonyl, wherein each occurrence of R is independently selected from the group consisting of H, C$_1$-C$_6$ alkyl, and C$_3$-C$_8$ cycloalkyl.

4. The compound of claim 1, wherein each occurrence of aryl or heteroaryl is independently optionally substituted with at least one substituent selected from the group consisting of C$_1$-C$_6$ alkyl, C$_1$-C$_6$ haloalkyl, C$_1$-C$_6$ haloalkoxy, halo, —CN, —OR, —N(R)(R), and C$_1$-C$_6$ alkoxycarbonyl, wherein each occurrence of R is independently selected from the group consisting of H, C$_1$-C$_6$ alkyl, and C$_3$-C$_8$ cycloalkyl.

5. The compound of claim 1, which is at least one selected from the group consisting of:

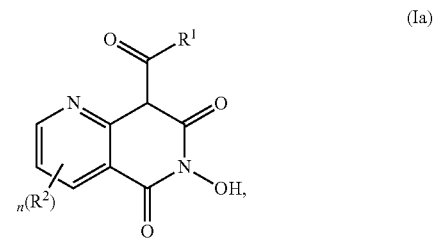

(Ia)

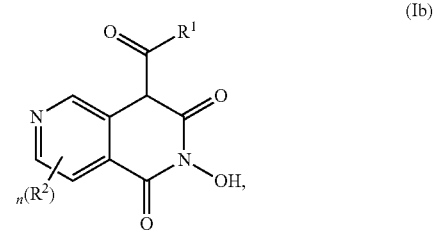

(Ib)

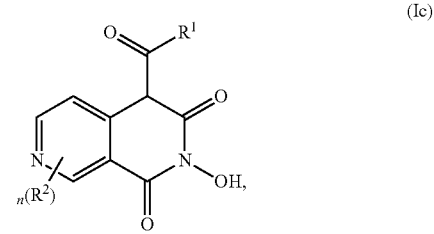

(Ic)

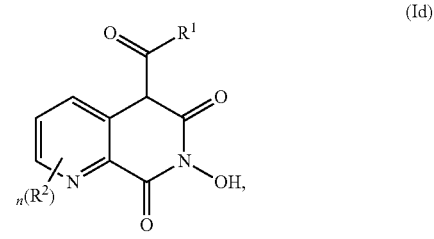

(Id)

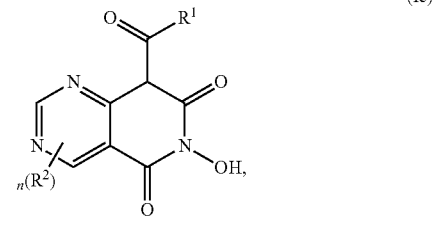

(Ie)

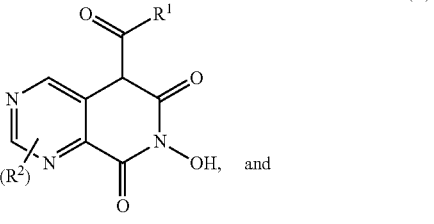

(If)

and

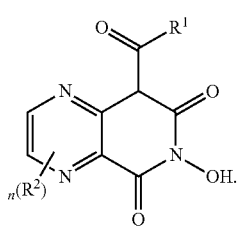

(Ig)

6. The compound of claim 1, which is:

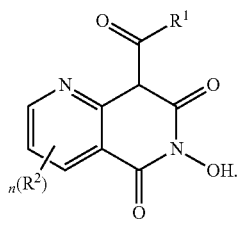

(Ia)

7. A compound selected from the group consisting of

Ethyl 6-hydroxy-2-methoxy-5,7-dioxo-5,6,7,8-tetrahydro-1,6-naphthyridine-8-carboxylate;

N,N-diethyl-6-hydroxy-2-methoxy-5,7-dioxo-5,6,7,8-tetrahydro-1,6-naphthyridine-8-carboxamide;

N-(4-chlorophenyl)-6-hydroxy-2-methoxy-5,7-dioxo-5,6,7,8-tetrahydro-1,6-naphthyridine-8-carboxamide;

N-(4-fluorophenyl)-6-hydroxy-2-methoxy-5,7-dioxo-5,6,7,8-tetrahydro-1,6-naphthyridine-8-carboxamide;

N-(4-Chlorobenzyl)-6-dihydroxy-2-methoxy-5,7-dioxo-5,6,7,8-tetrahydro-1,6-naphthyridine-8-carboxamide N-(4-fluorobenzyl)-2,6-dihydroxy-5,7-dioxo-5,6,7,8-tetrahydro-1,6-naphthyridine-8-carboxamide;

N-(4-Methoxybenzyl)-2,6-dihydroxy-5,7-dioxo-5,6,7,8-tetrahydro-1,6-naphthyridine-8-carboxamide;

or a salt, geometric isomer, stereoisomer, tautomer, or any mixtures thereof.

8. A pharmaceutical composition comprising at least one compound of claim 1 and a pharmaceutically acceptable carrier.

9. The pharmaceutical composition of claim 8, further comprising at least one additional agent useful for treating hepatitis B virus infection.

10. The pharmaceutical composition of claim 9, wherein the at least one additional agent comprises at least one selected from the group consisting of reverse transcriptase inhibitor; capsid inhibitor; cccDNA formation inhibitor; sAg secretion inhibitor;

oligomeric nucleotide targeted to the hepatitis B virus genome; and immunostimulator.

11. A method of treating hepatitis B virus infection in a subject, the method comprising administering to the subject a therapeutically effective amount of at least one compound of formula (I):

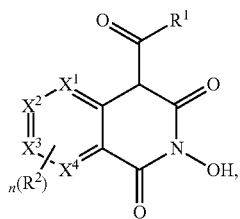

(I)

wherein:

R$^1$ is selected from the group consisting of —OR' and —NR'R', wherein each occurrence of R' is independently selected from the group consisting of H, optionally substituted C$_1$-C$_6$ alkyl, optionally substituted C$_2$-C$_6$ alkenyl, optionally substituted C$_2$-C$_6$ alkynyl, optionally substituted C$_3$-C$_8$ cycloalkyl, optionally substituted benzyl, optionally substituted aryl, and optionally substituted heteroaryl;

each of X$^1$, X$^2$, X$^3$, and X$^4$ is independently selected from the group consisting of N and CR$^3$, with the proviso that 1-2 of X$^1$, X$^2$, X$^3$, and X$^4$ are N;

each occurrence of R$^2$ and R$^3$ is independently selected from the group consisting of H, C$_1$-C$_6$ alkyl, C$_1$-C$_6$ haloalkyl, C$_1$-C$_6$ haloalkoxy, halo, —CN, —OR", —NR"R", —N(C$_0$-C$_6$ alkyl)C(=O)R", —N(C$_0$-C$_6$ alkyl)S(=O)$_2$R" —NO$_2$, —S(=O)$_2$NR"R", —OC(=O)R", and —C(=O )O—C$_1$-C$_6$ alkyl, wherein each occurrence of R" is independently selected from the group consisting of H, optionally substituted C$_1$-C$_6$ alkyl, optionally substituted C$_3$-C$_8$cycloalkyl, and optionally substituted phenyl; and n is 0, 1, 2, 3, or4;

or a salt, geometric isomer, stereoisomer, tautomer, or any mixtures thereof.

12. The method of claim 11, wherein the at least one compound is administered to the subject in a pharmaceutically acceptable composition.

13. The method of claim 11, wherein the subject is further administered at least one additional agent useful for treating the hepatitis B virus infection.

14. The method of claim 13, wherein the at least one additional agent comprises at least one selected from the group consisting of reverse transcriptase inhibitor;

capsid inhibitor; cccDNA formation inhibitor; sAg secretion inhibitor; oligomeric nucleotide targeted to the hepatitis B virus genome; and immunostimulator.

15. The method of claim 13, wherein the subject is co-administered the at least one compound and the at least one additional agent.

16. The method of claim 15, wherein the at least one compound and the at least one additional agent are coformulated.

17. A method of inhibiting RNAse H activity in a hepatitis B virus (HBV)-infected subject, the method comprising administering to the subject a therapeutically effective amount of at least one compound of formula (I):

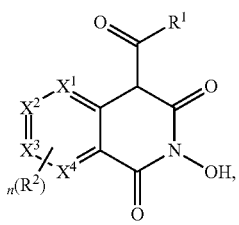

(I)

wherein:
R¹ is selected from the group consisting of —OR' and —NR'R', wherein each occurrence of R' is independently selected from the group consisting of H, optionally substituted $C_1$-$C_6$ alkyl, optionally substituted $C_2$-$C_6$ alkenyl, optionally substituted $C_2$-$C_6$ alkynyl, optionally substituted $C_3$-$C_8$ cycloalkyl, optionally substituted benzyl, optionally substituted aryl, and optionally substituted heteroaryl;

each of $X^1$, $X^2$, $X^3$, and $X^4$ is independently selected from the group consisting of N and $CR^3$, with the proviso that 1-2 of $X^1$, $X^2$, $X^3$, and $X^4$ are N;

each occurrence of $R^2$ and $R^3$ is independently selected from the group consisting of H, $C_1$-$C_6$ alkyl, $C_1$-$C_6$ haloalkyl, $C_1$-$C_6$ haloalkoxy, halo, —CN, —OR", —NR"R", —N($C_0$-$C_6$ alkyl)C(=O)R", —N($C_0$-$C_6$ alkyl)S(=O)$_2$R", —NO$_2$, —S(=O)$_2$NR"R", —OC(=O)R", and —C(=O)O—$C_1$-$C_6$ alkyl, wherein each occurrence of R" is independently selected from the group consisting of H, optionally substituted $C_1$-$C_6$ alkyl, optionally substituted $C_3$-$C_8$ cycloalkyl, and optionally substituted phenyl; and n is 0, 1, 2, 3, or 4;

or a salt, geometric isomer, stereoisomer, tautomer, or any mixtures thereof.

18. The method of claim 17, wherein the at least one compound is administered to the subject in a pharmaceutically acceptable composition.

19. The method of claim 17, wherein the subject is further administered at least one additional agent useful for treating the HBV infection.

20. The method of claim 19, wherein the at least one additional agent comprises at least one selected from the group consisting of reverse transcriptase inhibitor; capsid inhibitor; cccDNA formation inhibitor; sAg secretion inhibitor; oligomeric nucleotide targeted to the hepatitis B virus genome; and immunostimulator.

21. The method of claim 19, wherein the subject is co-administered the at least one compound and the at least one additional agent.

22. The method of claim 21, wherein the at least one compound and the at least one additional agent are coformulated.

23. The method of claim 11, wherein the subject is a mammal.

24. The method of claim 23, wherein the mammal is a human.

* * * * *